(12) United States Patent
Shi et al.

(10) Patent No.: US 10,774,079 B2
(45) Date of Patent: Sep. 15, 2020

(54) QUINAZOLINE DERIVATIVE

(71) Applicant: CSPC ZHONGQI PHARMACEUTICAL TECHNOLOGY (SHIJIAZHUANG) CO., LTD., Shijiazhuang (CN)

(72) Inventors: Ying Shi, Shijiazhuang (CN); Qingzhi Gao, Shijiazhuang (CN); Xiaozhuo Chen, Shijiazhuang (CN); Yi Mi, Shijiazhuang (CN); Yaran Zhang, Shijiazhuang (CN); Hanyu Yang, Shijiazhuang (CN); Yujie Chen, Shijiazhuang (CN); Chunlei Liu, Shijiazhuang (CN); Guorui Mi, Shijiazhuang (CN); Yuxiu Ma, Shijiazhuang (CN); Dongmin Shen, Shijiazhuang (CN); Yang Guo, Shijiazhuang (CN); Linjing Fan, Shijiazhuang (CN)

(73) Assignee: CSPC ZHONGQI PHARMACEUTICAL TECHNOLOGY (SHIJIAZHUANG) CO., LTD., Shijiazhuang (CN)

( * ) Notice: Subject to any disclaimer, the term of this patent is extended or adjusted under 35 U.S.C. 154(b) by 0 days.

(21) Appl. No.: 16/535,489

(22) Filed: Aug. 8, 2019

(65) Prior Publication Data
US 2019/0367500 A1 Dec. 5, 2019

Related U.S. Application Data

(62) Division of application No. 15/503,323, filed as application No. PCT/CN2015/000582 on Aug. 11, 2015, now Pat. No. 10,421,754.

(30) Foreign Application Priority Data

Aug. 11, 2014 (CN) .......................... 2014 1 0391653

(51) Int. Cl.
| C07D 417/12 | (2006.01) |
| C07D 403/12 | (2006.01) |
| C07D 239/94 | (2006.01) |
| A61P 35/00 | (2006.01) |
| A61K 31/517 | (2006.01) |
| C07D 401/12 | (2006.01) |
| C07D 405/12 | (2006.01) |
| C07D 413/14 | (2006.01) |

(52) U.S. Cl.
CPC .......... *C07D 417/12* (2013.01); *A61K 31/517* (2013.01); *A61P 35/00* (2018.01); *C07D 239/94* (2013.01); *C07D 401/12* (2013.01); *C07D 403/12* (2013.01); *C07D 405/12* (2013.01); *C07D 413/14* (2013.01)

(58) Field of Classification Search
CPC .................................................. C07D 417/12
See application file for complete search history.

(56) References Cited

U.S. PATENT DOCUMENTS

2017/0226099 A1    8/2017  Shi et al.

FOREIGN PATENT DOCUMENTS

| CN | 1205694 A | 1/1999 |
| CN | 1211239 A | 3/1999 |
| CN | 1212684 A | 3/1999 |
| CN | 1863534 A | 11/2006 |
| CN | 1882577 A | 12/2006 |
| CN | 101838245 A | 9/2010 |
| CN | 102532107 A | 7/2012 |
| CN | 102617463 A | 8/2012 |
| WO | 97/22596 A1 | 6/1997 |
| WO | 97/30035 A1 | 8/1997 |
| WO | 97/32856 A1 | 9/1997 |
| WO | 98/13354 A1 | 4/1998 |
| WO | 2004/006846 A2 | 1/2004 |
| WO | 2004/013633 A2 | 2/2004 |
| WO | 2009/094210 A1 | 7/2009 |

OTHER PUBLICATIONS

Pinedo et al. (2000).*
McMahon et al. (2000).*
Neidle et al. Cancer Drug Design & Discovery. (2008).*

(Continued)

*Primary Examiner* — Paul V Ward
(74) *Attorney, Agent, or Firm* — Kilpatrick Townsend & Stockton LLP

(57) ABSTRACT

Provided are a quinazoline derivative, a pharmaceutical composition containing the same, a method for preparation of said derivative, and an application of same as an anticancer drug.

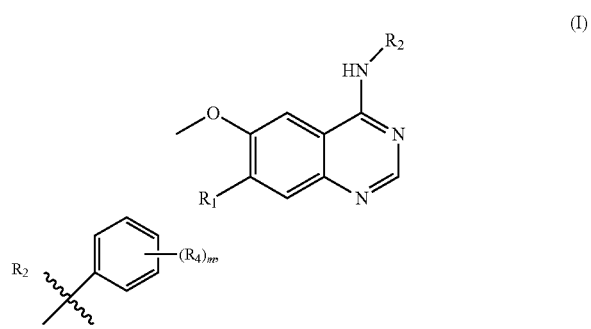

9 Claims, No Drawings

(56) References Cited

OTHER PUBLICATIONS

Database Registry [Online], Chemical Abstracts Service, Columbus, Ohio, US, Accession # 1356905-13-9, Feb. 16, 2012, 1 page.
Database Registry [Online], Chemical Abstracts Service, Columbus, Ohio, US, Accession # 13569005-14-0, Feb. 16, 2012, 1 page.
U.S. Appl. No. 15/503,323 , "Final Office Action", dated Jan. 30, 2019, 30 pages.
U.S. Appl. No. 15/503,323 , "Non-Final Office Action", dated Jul. 19, 2018, 9 pages.
U.S. Appl. No. 15/503,323 , "Non-Final Office Action", dated Nov. 2, 2017, 9 pages.
U.S. Appl. No. 15/503,323 , "Notice of Allowance", dated May 6, 2019, 5 pages.
U.S. Appl. No. 15/503,323 , "Notice of Allowance", dated Mar. 8, 2018, 6 pages.
U.S. Appl. No. 15/503,323 , "Restriction Requirement", dated Aug. 22, 2017, 5 pages.
U.S. Appl. No. 15/503,323 , "Restriction Requirement", dated Jun. 12, 2017, 5 pages.
Chen et al., "Elucidating inhibitory models of the inhibitors of epidermal growth factor receptor by docking and 3D-QSAR", Bioorganic & Medicinal Chemistry, vol. 12, Issue 9, 2004, pp. 2409-2417.
European Search Report issued in EP Application No. 15832452 dated Feb. 2, 2018, 10 pages.
Gao et al., "Radiosynthesis of [11C] Vandetanib and [11C]chloro-Vandetanib as new potential PET agents for imaging of VEGFR in cancer", Bioorg Med Chem Lett., vol. 21, issue 11, 2011, pp. 3222-3226.
Garofalo et al., "Synthesis and Structure—Activity Relationships of (Aryloxy)quinazoline Ureas as Novel, Potent, and Selective Vascular Endothelial Growth Factor Receptor-2 Inhibitors", Journal of Medicinal Chemistry, vol. 55, 2012, pp. 1189-1204.
Hennequin et al., "Design and Structure-Activity Relationship of a New Class of Potent VEGF Receptor Tyrosine Kinase Inhibitors", J. Med. Chem., vol. 42, issue 26, 1999, pp. 5369-5389.
McMahon et al., "VEGF Receptor Signaling in Tumor Angiogenesis", The Oncologist 2000; 5 (suppl 1): [www.TheOncologiest.com], pp. 3-10.
Neidle et al., "Cancer Drug Design and Discovery", First Edition, Elsevier/Academic Press, 2008.
International Search Report and Written Opinion issued in Application No. PCT/CN2015/000582 dated Nov. 20, 2015, 16 pages.
Pinedo et al., "Translational Research : The Role of VEGF in Tumor Angiogenesis", The Oncologist 2000; 5(suppl 1); [www.TheOncologist.com]., 2000, pp. 1-2.

* cited by examiner

QUINAZOLINE DERIVATIVE

CROSS REFERENCE TO RELATED APPLICATION

This application is a divisional of U.S. patent application Ser. No. 15/503,323 filed Feb. 10, 2017, which is a national stage application under 35 U.S.C. § 371 of PCT/CN2015/000582 filed Aug. 11, 2015, which claims priority to Chinese Application No. 201410391653.7 filed Aug. 11, 2014, the disclosures of each which are hereby incorporated by reference herein in their entireties.

TECHNICAL FIELD

The present invention relates to quinazoline derivatives, pharmaceutical compositions, preparation methods and pharmaceutical uses thereof.

BACKGROUND ART

Kinases are essential cellular signaling molecules. Mutations in kinases can lead to diseases or conditions including immunodeficiencies, cancers, cardiovascular diseases and endocrine disorders, such as Parkinson's disease, metabolic diseases, tumorigenesis, Alzheimer's disease, heart disease, diabetes, neurodegeneration, inflammation, kidney disease, atherosclerosis and airway disease.

Cancers result from deregulated signaling pathways that mediate cell growth and programmed cell death (apoptosis). Protein kinases are a large family of proteins that play an important role in signaling pathways that regulate a number of different cellular functions, such as cell growth, differentiation, and death.

Hyperactivity of protein kinases is implicated in a variety of human cancers. For example, the Akt2 kinase has been found to be over-expressed in ovarian tumors (J. Q. Cheung et al., Proc. Natl. Acad. Sci. U.S.A. 89: 9267-9271 (1992)) and pancreatic cancers (J. Q. Cheung et al., Proc. Natl. Acad. Sci. U.S.A. 93: 3636-3641 (1996)), and the Akt3 kinase was found to be over-expressed in breast and prostate cancer cell lines (Nakatani et al., J. Biol. Chem. 274: 21528-21532 (1999)).

Various protein kinase inhibitors have been shown to effectively treat certain cancers. For example, Gleevec™ (imantinib, Novartis), can be used to treat chronic myeloid leukemia (CML) (Kumar et al.), and a Raf kinase inhibitor (BAY-43-9006) has been evaluated for treating solid tumors and myeloid leukemia (WO 2004/022562).

Tyrosine kinase is a group of enzymes for catalyzing phosphorylation of protein tyrosine residues, and it plays a critical role in endocellular signal transduction. Tyrosine kinase participates in the regulation of normal cells, signal transmission and development, as well as associates with proliferation, differentiation, migration and apoptosis of tumor cell. Dysfunction of tyrosine kinase can cause the disorder of cell proliferation, leading to the formation of tumor eventually.

Tyrosine kinases for many receptors are involved in the formation of tumor, the reasons of which include gene mutation, chromosome translocation or kinase over-expression.

Tyrosine kinase inhibitors are designed according to the structures of the protein tyrosine kinases, and most of them belong to competitive inhibitors of ATP (adenosine triphosphate). These inhibitors act on the intracellular kinase region of tyrosine protein kinase, so as to inherently block the downstream signal transduction mediated by tyrosine kinase, and therefore inhibit the growth, angiogenesis and metastasis of tumor.

Vandetanib is a synthesized aniline-quinazoline compound, which can act on tyrosine kinases for VEGFR, EGFR and RET of the tumor cells simultaneously, and also can selectively inhibit other tyrosine kinases as well as serine/threonine kinases.

Therefore, target drugs that can inhibit the protein kinase represent a new generation of chemotherapeutic agents for the specific molecule objects. And they have the potential to provide greater efficacy in the treatment of various cancers with fewer side effects than conventional chemotherapeutic agents.

SUMMARY OF THE INVENTION

In one aspect, the present invention provides a compound of formula (I) or a pharmaceutically acceptable salt thereof:

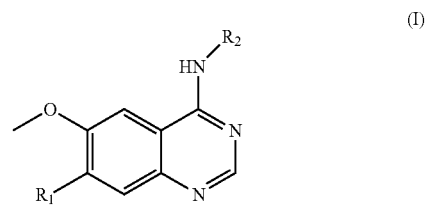

wherein $R_1$ is —O(CH$_2$)$_n$R$_3$, wherein n is 0, 1, 2, 3, 4 or 5, $R_3$ is:

(1) aryl, such as phenyl, optionally substituted by $R^a$ and/or $R^b$, wherein $R^a$ and $R^b$ are each independently selected from a group consisting of haloalkyl such as trifluoromethyl, cyano, and saturated heterocycloalkyl, such as saturated heterocycloalkyl containing one or more heteroatoms selected from O, N and S, for instance morpholino, or $R^a$ and $R^b$ are taken together to form —O—CH$_2$—O—;

(2) heteroaryl optionally substituted by $R^c$ and/or $R^d$, wherein $R^c$ and $R^d$ are each independently selected from a group consisting of alkyl, and saturated heterocycloalkyl-carbonyl, such as saturated heterocycloalkyl-carbonyl containing one or more heteroatoms selected from O, N and S, for instance morpholino-carbonyl;

(3) —NR$^e$R$^f$, wherein $R^e$ and $R^f$ are each independently selected from a group consisting of hydrogen and alkyl, with the proviso that they are not both hydrogen, or $R^e$ and $R^f$ are taken together to form —(CH$_2$)$_4$—;

(4) —CONR$^g$R$^h$, wherein $R^g$ and $R^h$ are each independently selected from a group consisting of hydrogen and alkyl; or (5) saturated heterocycloalkyl, such as tetrahydropyrane; and R$_2$ is

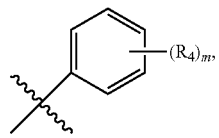

wherein
R$_4$ is independently selected from F, Cl and Br; and m=2.

In another aspect, the present invention provides a pharmaceutical composition, comprising the compound of formula (I) or a pharmaceutically acceptable salt thereof.

In another aspect, the present invention provides a use of the compound of formula (I) or a pharmaceutically acceptable salt thereof in the manufacture of a medicament for the treatment of cancer, such as thyroid cancer, non-small cell carcinoma, epidermoid carcinoma, melanoma, colon cancer, gastric carcinoma, esophagus cancer, pancreatic carcinoma, renal carcinoma, liver cancer, lung cancer or ovarian cancer.

In a further aspect, the present invention provides a method for preparing the compound of formula (I) or a pharmaceutically acceptable salt, the method comprises reacting a compound of formula (III) or its salt with a compound of formula (IV) or its salt in a solvent and optionally in the presence of one or more of a catalyst, a base and a surfactant, to obtain the compound of formula (I):

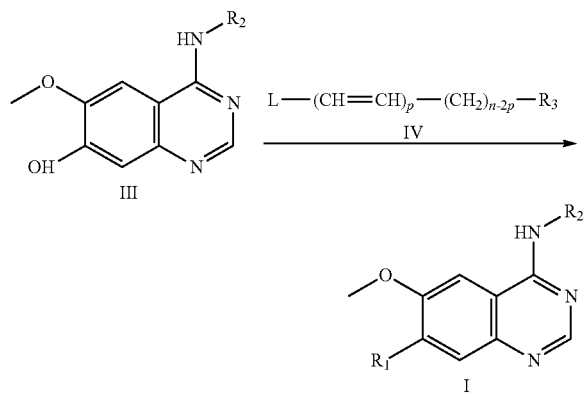

wherein:
R$_1$, R$_2$, R$_3$ and n are as defined in claim 1;
L represents halogen, hydroxyl, mesyloxy or hydrogen; and
p=0 or 1, with the proviso that when p is 1, L is hydrogen.

DETAILED DESCRIPTION OF THE INVENTION

Terms and Definitions

As used in the specification and the attached claims, unless specified to the contrary, the following terms have the meaning indicated:

The term "alkyl" used herein denotes straight or branded chain saturated hydrocarbon radical containing 1-10 carbon atoms. The term "C$_{1-6}$ alkyl" denotes straight or branded chain saturated hydrocarbon radical containing 1-6 carbon atoms. The representative examples of alkyl include but are not limited to: methyl, ethyl, n-propyl, isopropyl, n-butyl, sec-butyl, isobutyl, tertiary butyl, n-pentyl, isopentyl, neopentyl, n-hexyl, 3-methylhexyl, 2,2-dimethyl pentyl, 2,3-dimethyl pentyl, n-heptyl, n-octyl, n-nonyl and n-decyl.

The term "saturated heterocycloalkyl" used herein denotes monocyclic or bicyclic saturated heterocycloalkyl without double bond and/or triple bond. The ring atomic number of saturated heterocycloalkyl may be 3, 4, 5, 6, 7 or 8. In addition to carbon atom, the ring atoms may contain 1, 2 or 3 heteroatoms independently selected from N, O and S. The examples of saturated heterocycloalkyl include but are not limited to azetidinyl, 1,3-dioxanyl, 1,3-dithiacyclohexanyl, 1,3-dithiacyclopentyl, 1,3-dioxolanyl, 1,2-thiazinyl, 1,3-thiazinyl, aziridinyl, pyrrolidyl, pyrazolidinyl, azepanyl, oxazolidinyl, oxadiazolidinyl, diazepanyl, imidazolidinyl, piperidyl, piperazinyl, thiazolidinyl, thiadiazolidinyl, tetrahydropyranyl, tetrahydrofuranyl, tetrahydrothiophenyl, isoxazolidinyl, isothiazolidinyl and trithianyl. The saturated heterocycloalkyl in the present invention attaches to the core structure through any carbon atom or any nitrogen atom on the ring, and it can be substituted or unsubstituted.

The term "aryl" used herein denotes phenyl or naphthyl.

The term "heteroaryl" used herein denotes a 5- or 6-membered monocyclic and 9- or 10-membered bicyclic heteroaryl, and it can contain 1, 2 or 3 heteroatoms independently selected from N, O and S. The representative examples of monocyclic heteroaryl include but are not limited to furyl, imidazolyl, isoxazolyl, isothiazolyl, oxadiazolyl, 1,3-oxazolyl, pyridinyl, pyridazinyl, pyrimidinyl, pyrazinyl, pyrrolyl, pyrazolyl, tetrazolyl, thiadiazolyl, 1,3-thiazolyl, thiophenyl, triazolyl, and triazinyl. The representative examples of bicyclic heteroaryl include but are not limited to benzofuranyl, benzothiophenyl, benzoxazolyl, benzimidazolyl, benzoxadizolyl, 6,7-dihydro-1,3-benzothiazolyl, imidazo[1,2-a]pyridinyl, indazolyl, indolyl, isoindolyl, isoquinolyl, naphthyridinyl, pyridimidazolyl, quinolyl, thiazolo[5,4-b]pyridine-2-yl, thiazolo[5,4-b]pyrimidine-2-yl, and 5,6,7,8-tetrahydroquinoline-5-yl. The monocyclic and bicyclic heteroaryl in the present invention may be substituted or unsubstituted, and attaches to the core structure through any carbon atom or nitrogen atom on ring.

The term "carbonyl" used herein denotes —CO—.

The term "cyano" used herein denotes —CN.

The term "halogen" or "halo" used herein denotes Cl, Br, I or F.

The term "haloalkyl" used herein denotes the alkyl as defined herein, on which 1, 2, 3, 4, 5 or 6 hydrogen atoms are replaced with halogen. The representative examples of haloalkyl include but are not limited to chloromethyl, 2-fluoroethyl, 2,2,2-trifluoroethyl, trifluoromethyl, difluoromethyl, pentafluoroethyl, 2-chloro-3-fluoropentyl and trifluoropropyl, such as 3,3,3-trifluoro-propyl.

The term "heteroatom" used herein includes N, O and S.

The term "salt" used herein includes hydrochloride, hydrobromide, sulfate, sulfite, phosphate, mesylate, p-tosylate, maleate, tartrate, malate, fumarate, citrate, trifluoroacetate and the like.

Compounds of the Invention

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95% 99%, and still more preferably an excess greater than about 99%. Accordingly, this invention includes racemic mixtures, relative and absolute stereoisomers, and mixtures of relative and absolute stereoisomers.

Compounds of this invention containing NH, C(O)OH, OH or SH moieties may have attached there to prodrug forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. References that may be mentioned include, for instance, Lizondo, J et al., Drugs Fut, 21(11), 1116 (1996); Brickner, S J et al., J Med Chem, 39(3), 673 (1996); Mallesham, B et al., Org Lett, 5(7), 963 (2003).

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic. Kushner et al., Can. J. Physiol. Pharmacol., 77, 79-88 (1999); Foster et al., Advances in Drug Research Vol. 14, pp. 2-36, Academic press, London, 1985; Kato et al., J. Labelled Comp. Radiopharmaceut., 36(10):927-932 (1995).

In addition, non-radioactive isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

Stable isotope labeling of a drug can alter its physico-chemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-istopic compound.

Amides, Esters and Prodrugs

Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hem i-aminals, polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Esters can be prepared from substrates containing either a hydroxyl group or a carboxyl group by general methods known to persons skilled in the art. The typical reactions of these compounds are substitutions replacing one of the heteroatoms by another atom. Amides can be prepared from substrates containing either an amino group or a carboxyl group in similar fashion. Esters can also react with amines or ammonia to form amides. Another way to make amides is to heat carboxylic acids and amines together.

The present invention provides a compound of formula (I) or a pharmaceutically acceptable salt thereof:

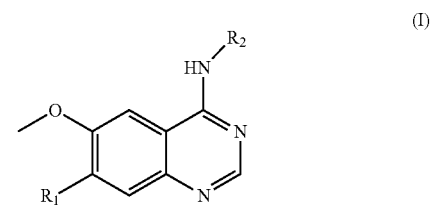

wherein
R₁ is —O(CH₂)ₙR₃,
   wherein
   n is 0, 1, 2, 3, 4 or 5,
   R₃ is:
   (1) aryl, such as phenyl, optionally substituted by $R^a$ and/or $R^b$, wherein $R^a$ and $R^b$ are each independently selected from a group consisting of haloalkyl such as trifluoromethyl, cyano, and saturated heterocycloalkyl, such as saturated heterocycloalkyl containing one or more heteroatoms selected from O, N and S, for instance morpholino or $R^a$ and $R^b$ are taken together to form —O—CH₂—O—;
   (2) heteroaryl, optionally substituted by $R^c$ and/or $R^d$, wherein $R^c$ and $R^d$ are each independently selected from a group consisting of alkyl, and saturated heterocycloalkyl-carbonyl, such as saturated heterocycloalkyl-carbonyl containing one or more heteroatoms selected from O, N and S, for instance morpholino-carbonyl;
   (3) —NR$^e$R$^f$,
   wherein $R^e$ and $R^f$ are each independently selected from a group consisting of hydrogen and alkyl, with the proviso that they are not both hydrogen, or $R^e$ and $R^f$ are taken together to form —(CH₂)₄—;
   (4) —CONR$^g$R$^h$,
   wherein $R^g$ and $R^h$ are each independently selected from a group consisting of hydrogen and alkyl; or
   (5) saturated heterocycloalkyl, such as tetrahydropyrane; and

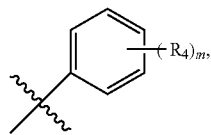

R₂ is
   wherein
   R₄ is independently selected from F, Cl and Br; and
   m=2.
   In one embodiment, said R₂ is

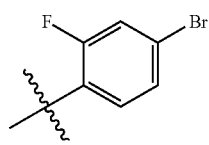 or 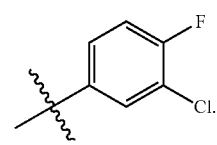

In one embodiment, said aryl is phenyl or naphthyl.

In one embodiment, said saturated heterocycloalkyl is a 5- to 7-membered saturated heterocycloalkyl containing 1, 2 or 3 heteroatoms independently selected from O, N and S.

In one embodiment, said heteroaryl is a monocyclic or bicyclic heteroaryl, preferably, it's a 5- or 6-membered monocyclic or 9- or 10-membered bicyclic heteroaryl containing 1, 2 or 3 heteroatoms independently selected from O, N and S, more preferably, it's pyridinyl, imidazolyl, thiazolyl or benzimidazolyl.

In one embodiment, said alkyl is $C_{1-6}$ alkyl.

In one embodiment, said R₁ is selected from:

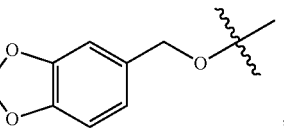,

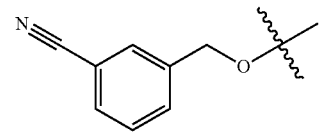,

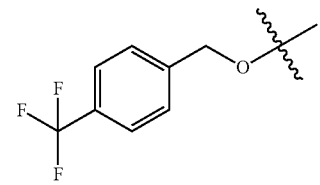,

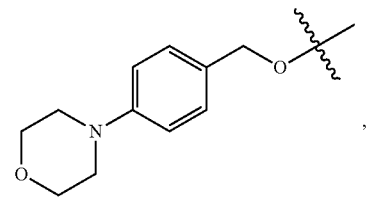,

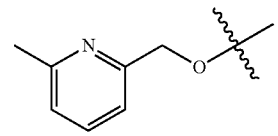,

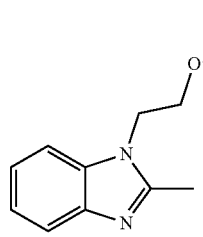 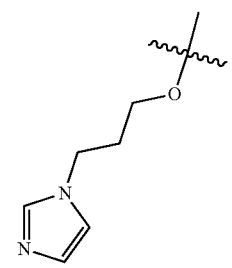,

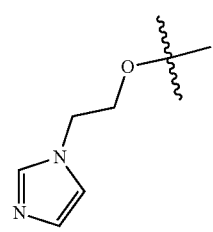 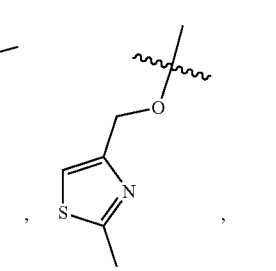,

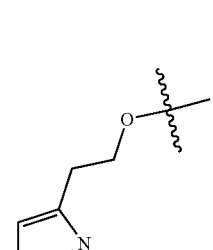 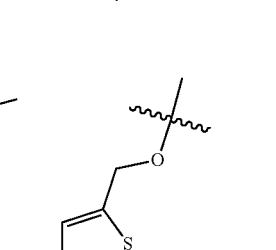

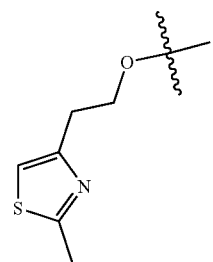 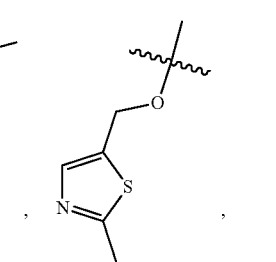

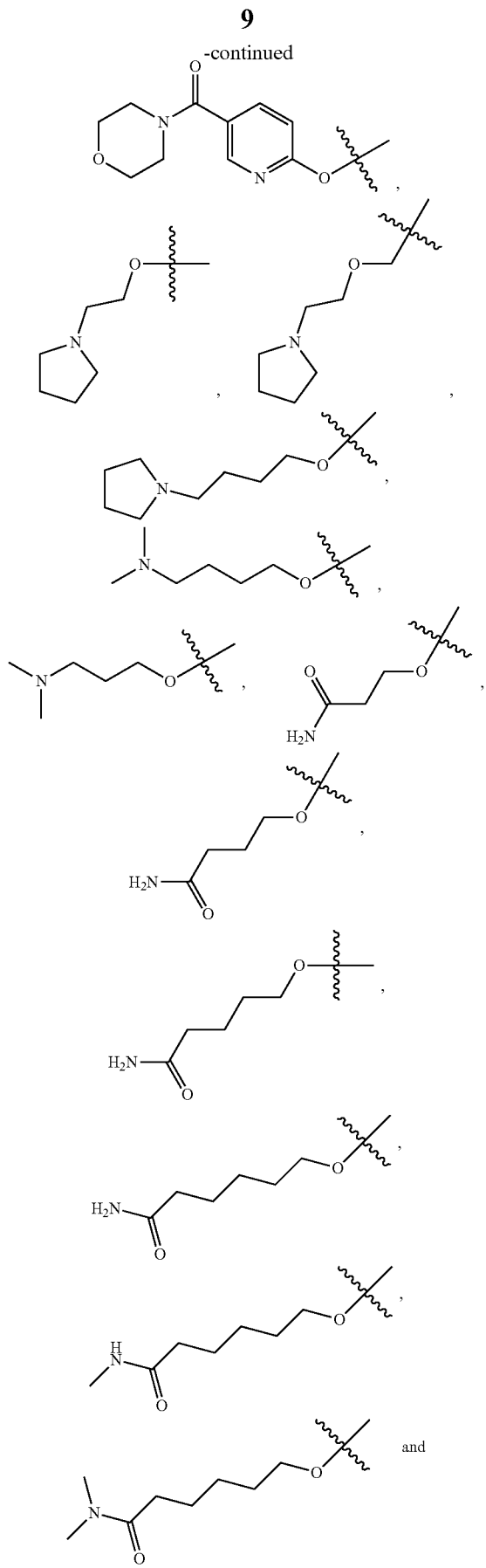

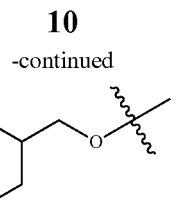

In the compounds of formula (I), $R_1$, $R_2$, $R_3$, $R_4$, $R^a$, $R^b$, $R^c$, $R^d$, $R^e$, $R^f$, $R^g$, $R^h$, m and n can be independently and appropriately selected. The embodiments described herein can be combined, and any combination of embodiments can be within the scope of this invention. For instance, an embodiment, in which any of $R_1$, $R_2$, $R_3$, $R_4$, $R^a$, $R^b$, $R^c$, $R^d$, $R^e$, $R^f$, $R^g$, $R^h$, m and n are defined, and another embodiment, in which any of $R_1$, $R_2$, $R_3$, $R_4$, $R^a$, $R^b$, $R^c$, $R^d$, $R^e$, $R^f$, $R^g$, $R^h$, m and n are defined, can be combined to form a new embodiment. If the new embodiment is not null, it should be considered as being specifically disclosed in the present application and constitute a part of the present invention.

In one embodiment, the present invention provides a compound of formula (I) selected from the followings, or a pharmaceutically acceptable salt thereof:

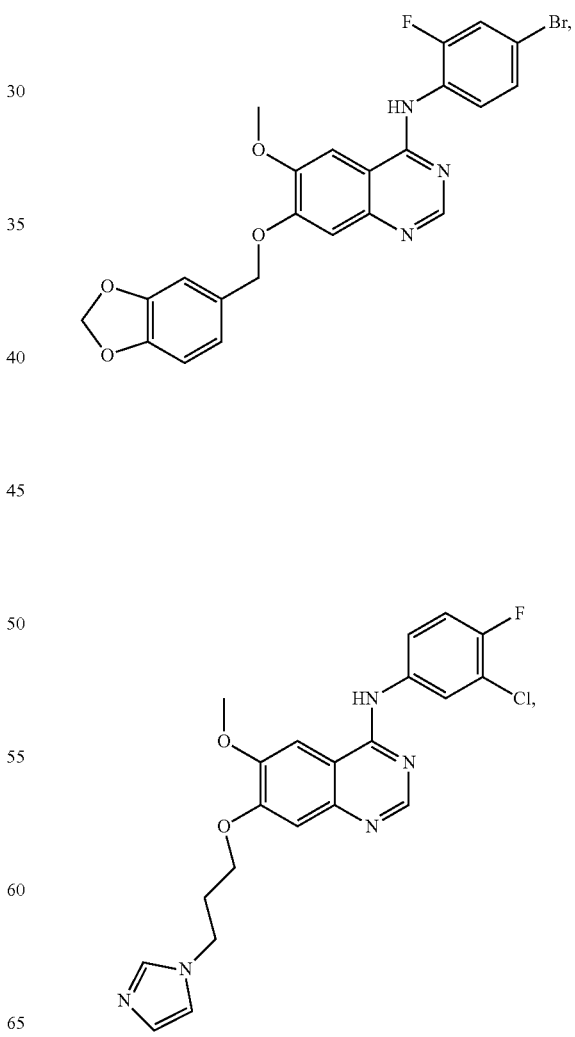

-continued
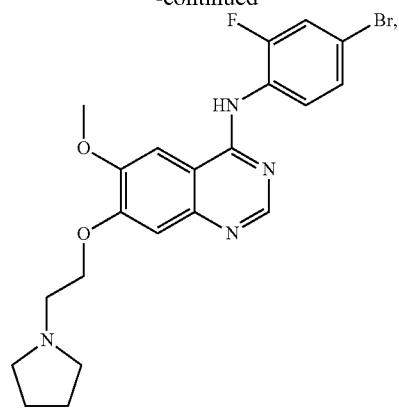
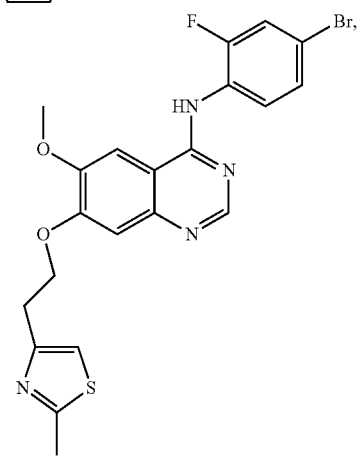
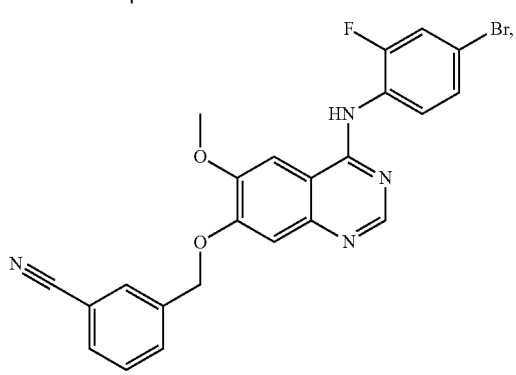
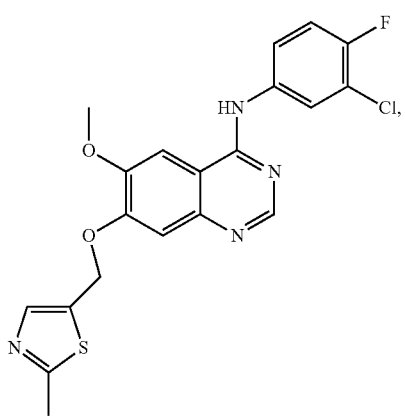
-continued
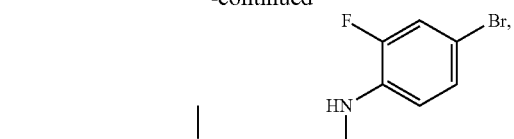
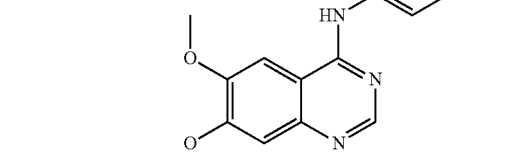
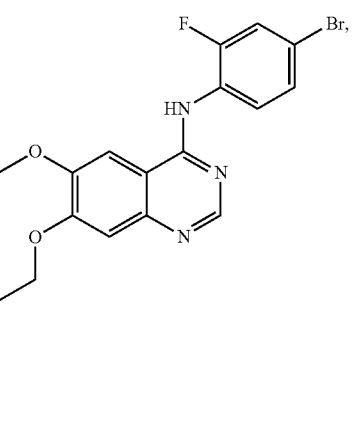

-continued
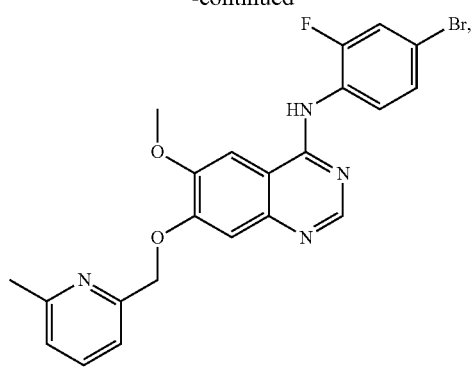
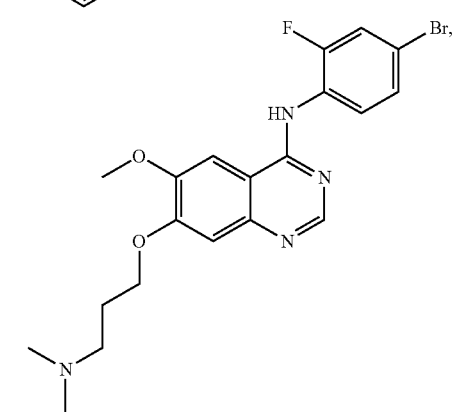
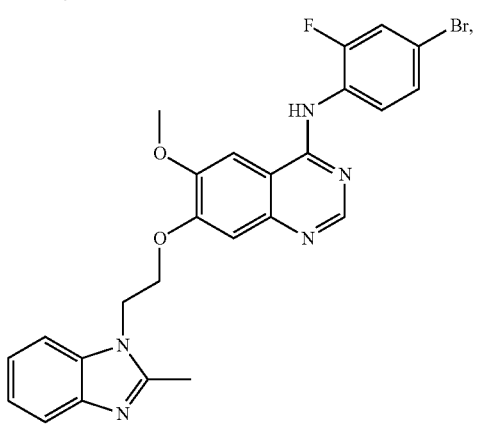
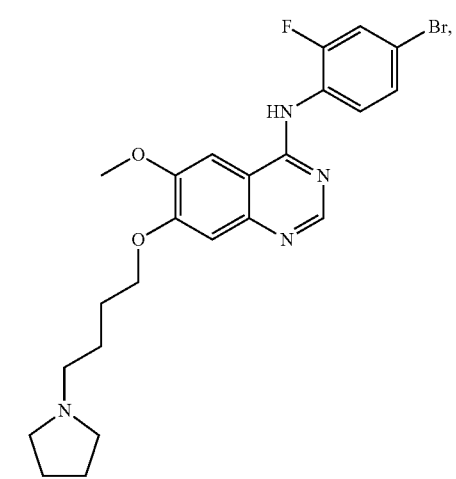
-continued
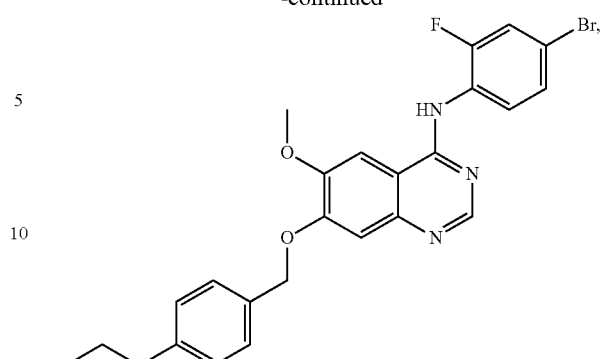
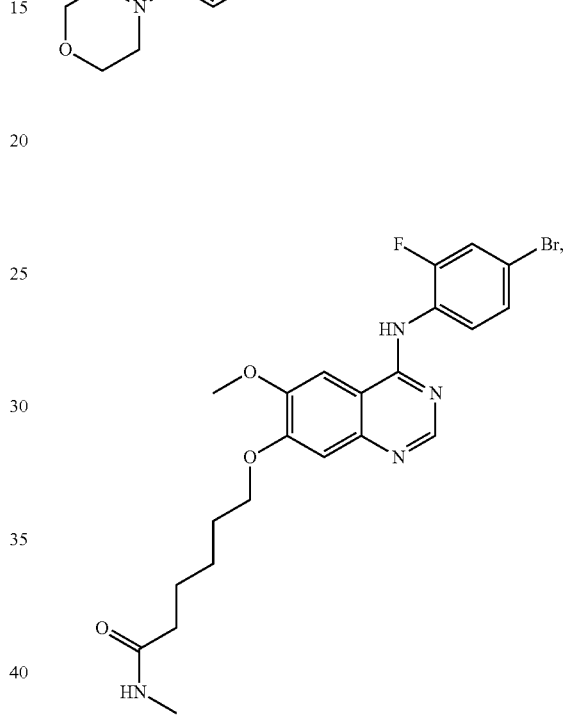
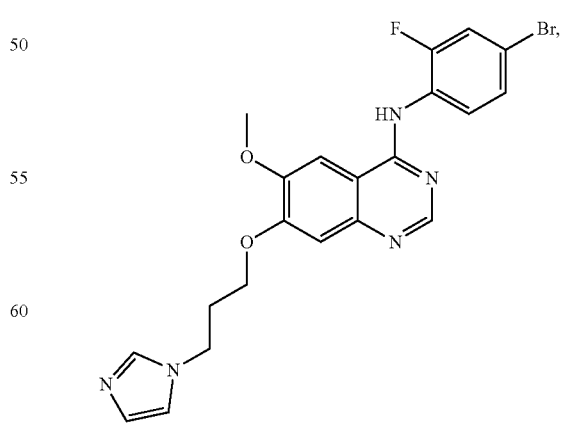

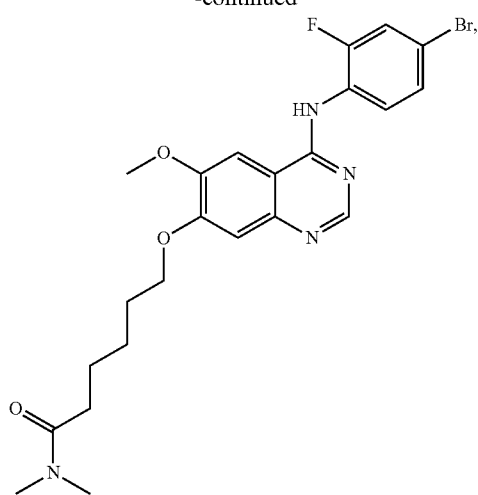
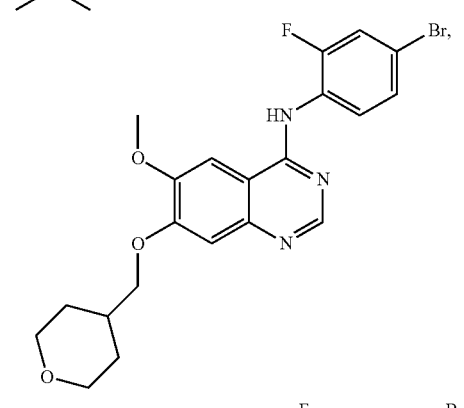
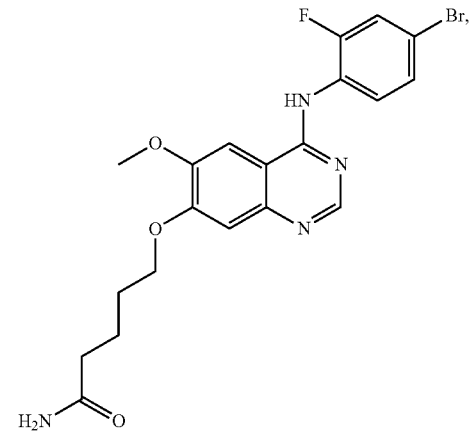
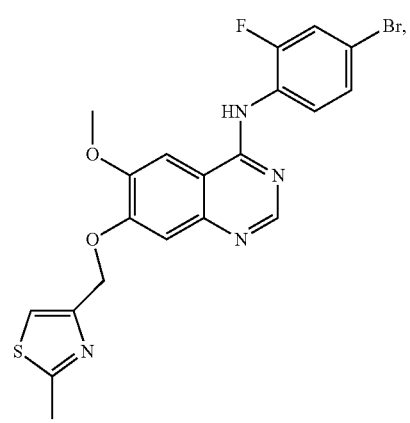
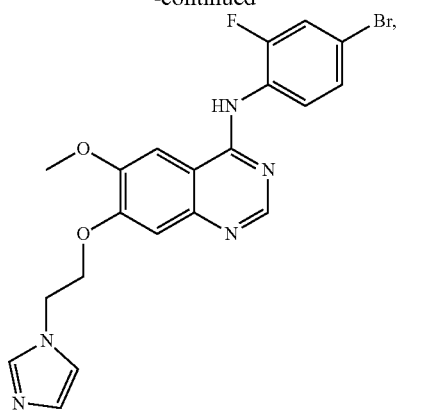
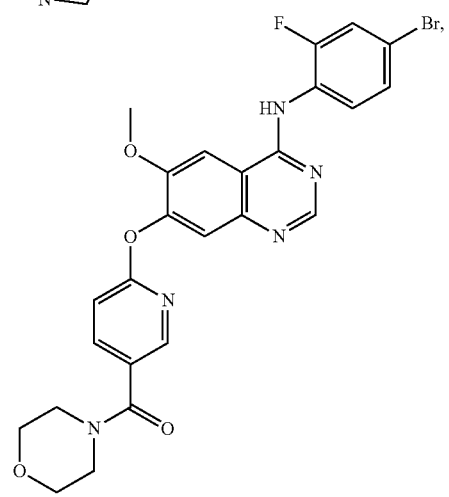
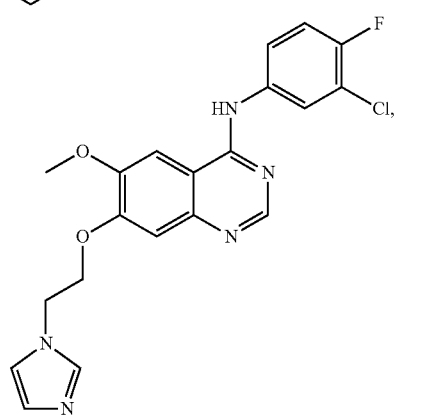
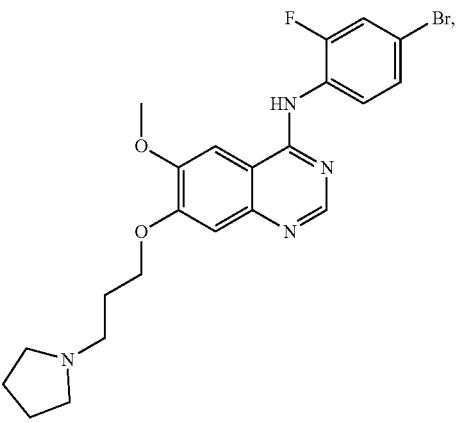

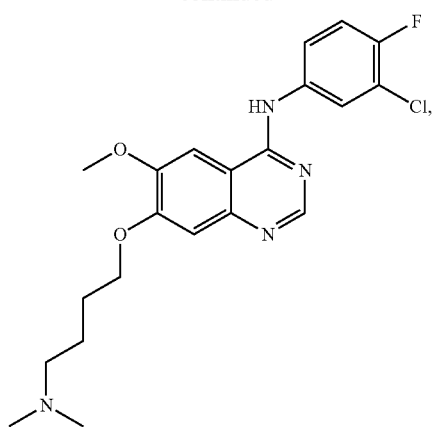
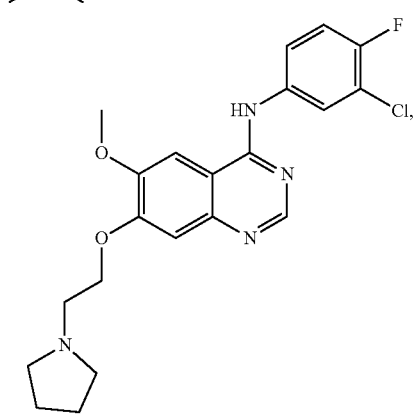
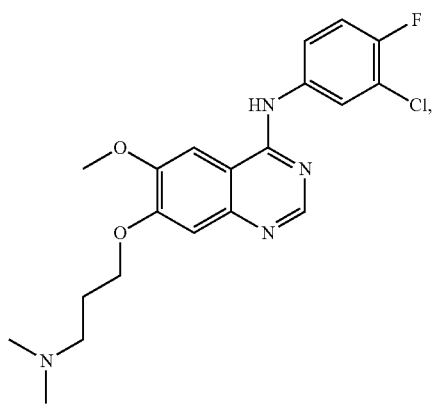
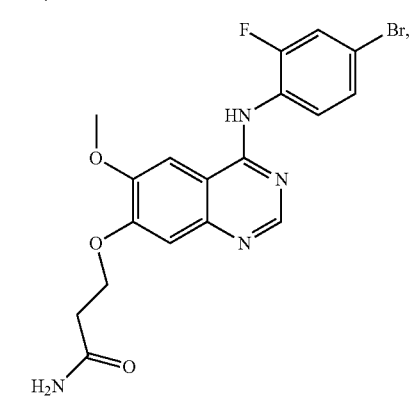
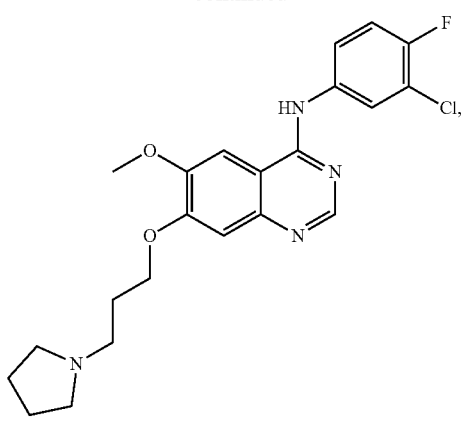
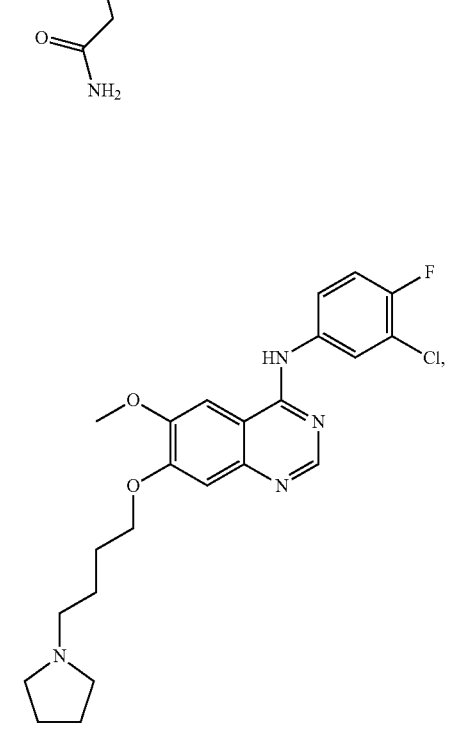
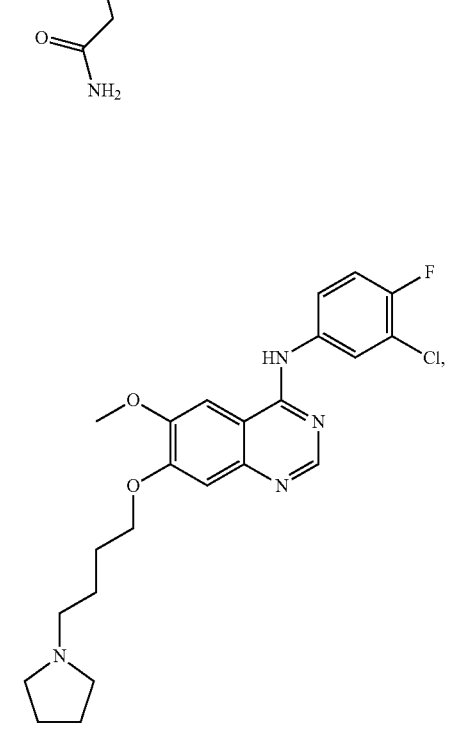

-continued

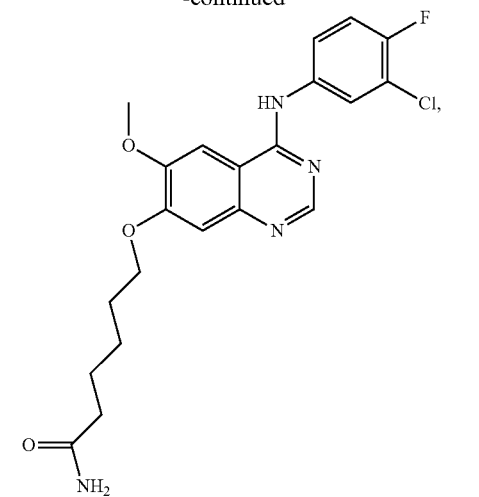

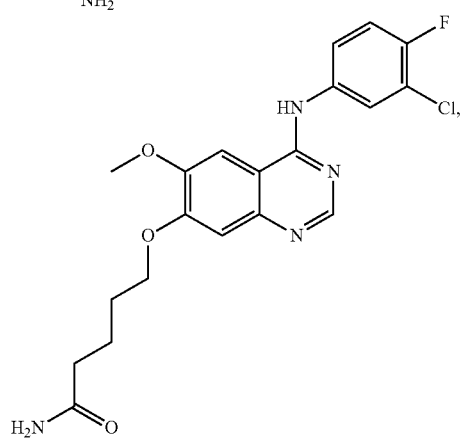

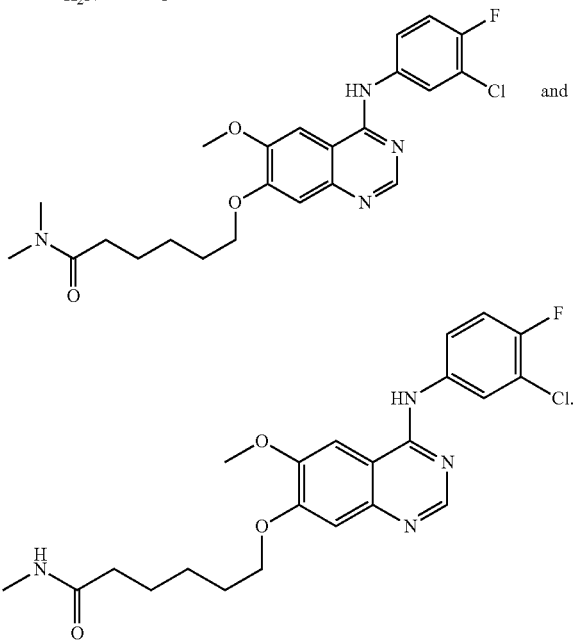

Pharmaceutical Compositions

The present invention also provides a pharmaceutical composition containing the compound of formula (I) and a pharmaceutically acceptable salt thereof.

The pharmaceutical composition can be administered by oral route, e.g. in the form of granules, tablets or capsules, or by parenteral injection, e.g. intravenous injection, subcutaneous injection, intramuscular injection or intrathecal injection, or by transfusion e.g. in the form of sterile solutions, suspensions or emulsion, or by local application, e.g. in the form of ointment or cream, or by rectally administration, e.g. in form of suppository. Generally, the above-mentioned compositions can be prepared by conventional methods with conventional excipients.

The pharmaceutical composition of the present invention can be used for the treatment of tumors.

Medicinal Uses

The compound (including a pharmaceutically acceptable salt thereof) and the pharmaceutical composition of the invention can be used for the treatment of tumors, in particular, thyroid cancer, non-small cell carcinoma, epidermoid carcinoma, melanoma, colon cancer, liver cancer, lung cancer or ovarian cancer.

The present invention provides a method for the treatment of cancer or tumors, such as thyroid cancer, non-small cell carcinoma, epidermoid carcinoma, melanoma, colon cancer, gastric carcinoma, esophagus cancer, pancreatic carcinoma, renal carcinoma, liver cancer, lung cancer or ovarian cancer, comprising administering a therapeutically effect amount of the compound (including a pharmaceutically acceptable salt thereof) or the pharmaceutical composition of the present invention to a subject in need thereof.

The present invention, also provides a use of the compound (including a pharmaceutically acceptable salt thereof), or a pharmaceutical composition of the present invention in manufacture of a medicament for the treatment of cancer, such as thyroid cancer, non-small cell carcinoma, epidermoid carcinoma, melanoma, colon cancer, gastric carcinoma, esophagus cancer, pancreatic carcinoma, renal carcinoma, liver cancer, lung cancer or ovarian cancer.

Method of Preparation

The present invention also provides a method for preparing the compound or a pharmaceutically acceptable salt thereof, comprising reacting a compound of formula (III) or its salt with a compound of formula (IV) or its salt in a solvent and optionally in the presence of one or more of a catalyst, a base and a surfactant, to obtain the compound of formula (I),

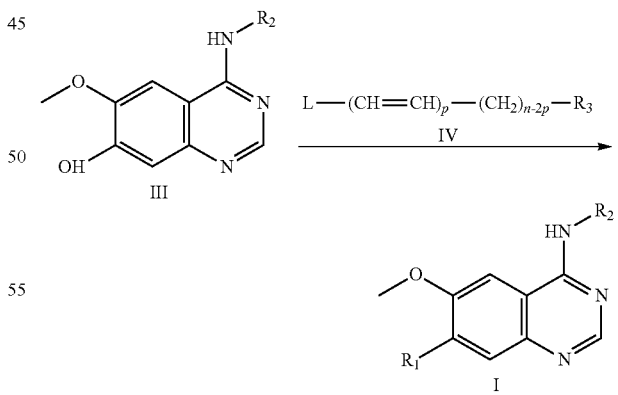

wherein $R_1$, $R_2$, $R_3$ and n are as defined in claim 1;

L represents halogen, hydroxyl, mesyloxy and hydrogen; and p=0 or 1, with the proviso that when p=1, L is hydrogen.

In a preferred embodiment of the present invention, the compound of formula (III) is the following formulae (III-1) or (III-2):

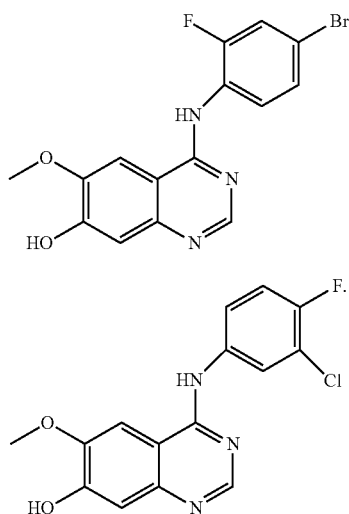

In one embodiment, the compounds of formula (I) are synthesized by the condensation of formula (III) and formula (IV) in a solvent, wherein the solvent is selected from:
water, or
an organic solvent, for instance:
an alcohol (e.g. methanol, ethanol, isopropyl alcohol and the like),
an ether (e.g. diethyl ether, methyl tert-butyl ether, tetrahydrofuran, 1,4-dioxane and the like),
an ester (e.g. ethyl acetate and the like),
an aromatichydrocarbon (e.g. toluene, xylene and the like),
a halogenated alkane (e.g. methylene chloride, chloroform, carbon tetrachloride and the like),
an aprotic solvent (e.g. acetone, butanone, acetonitrile, N,N-dimethylformamide (DMF), dimethyl sulfoxide, N-methyl pyrrolidone and the like), Preferably, the solvent is water, ethanol, tetrahydrofuran, toluene, methylene chloride, acetonitrile, N,N-dimethylformamide (DMF), dimethyl sulfoxide or N-methyl pyrrolidone.

More preferably, the solvent is tetrahydrofuran, methylenechloride, acetonitrile, N,N-dimethylformamide (DMF) or N-methyl pyrrolidone.

The reaction temperature is 0 to 200° C., preferably 10° C. to 150° C., more preferably 20° C. to 120° C.

The reaction time is 1-72 hours, preferably 2-48 hours.

In the above embodiment, in one case, a base is added in the reaction, wherein said base is selected from an organic base or an inorganic base.

The organic base is selected from triethylamine, N,N-diisopropylethylamine (DIPEA), pyridine, 4-dimethylaminopyridine, morpholine, N-methylmorpholine, 1,8-diazabicyclo(5.4.0)-undec-7-ene (DBU), 1,5-diazabicyclo[4.3.0]non-5-ene (DBN) and the like.

The inorganic base is selected from sodium carbonate, potassium carbonate, cesium carbonate, potassium hydroxide, sodium hydroxide, cesium hydroxide, lithium hydroxide, sodium hydride and the like.

Preferably, the base is selected from N,N-diisopropylethylamine (DIPEA), 1,8-diazabicyclo(5.4.0)-undec-7-ene (DBU), sodium carbonate, potassium carbonate, cesium carbonate, potassium hydroxide and sodium hydroxide.

More preferably, the base is selected from 1,8-diazabicyclo(5.4.0)-undec-7-ene (DBU), potassium carbonate and cesium carbonate.

In the above embodiment, in another case, a condensing agent is added in the reaction, wherein said condensing agent is selected from N,N'-dicyclo-hexylcarbodiimide (DCC), N,N'-diisopropylcarbodiimide (DIC) or 1-(3-dimethylaminopropyl)-3-ethylcarbodiimide hydrochloride (EDCl or EDCl.HCl). Preferably, the condensing agent is N,N'-dicyclohexylcarbodiimide (DCC).

In the above embodiment, in another case, to the reaction is added a catalyst, e.g. triphenylphosphine (PPh$_3$) or tributylphosphine, together with an azodicarbonyl derivative (such as diisopropyl azodicarboxylate (DIAD), diethyl azodicarboxylate (DEAD), di-tert-butyl azodicarboxylate (DBAD), azodicarboxylic dimorpholide (ADDM) and azodicarboxylic acid dipiperidide (ADDP)), or another catalyst (such as cuprous iodide, cuprous bromide, potassium iodide and sodium iodide). Preferably, the catalyst is triphenylphosphine, together with azodicarboxylic acid ester, cuprous iodide, potassium iodide or sodium iodide. More preferably, the catalyst is triphenylphosphine, together with diisopropyl azodicarboxylate (DIAD) or cuprous iodide.

In the above embodiment, in another case, to the reaction is added a surfactant, e.g. tetrabutylammonium chloride, tetrabutylammonium bromide, tetrabutylammonium iodide, tetrabutylammonium hydrogen sulfate or tetrabutylammonium hydroxide. Preferably, the surfactant is tetrabutylammonium bromide or tetrabutylammonium iodide. More preferably, the surfactant is tetrabutylammonium bromide.

Specifically, in a preferable embodiment, the method of preparing the compound of formula (I) or a pharmaceutically acceptable salt thereof comprises reacting the compound of formula (III) or its salt with the compound of formula (IV) or its salt in presence of a solvent and a catalyst.

For instance, the catalyst can be triphenylphosphine and diisopropyl azodicarboxylate (DIAD):

For instance, the compound of formula (III) (core structure), the compound of formula (IV) (side chain) and triphenylphosphine are dissolved in a solvent (e.g. anhydrous tetrahydrofuran) at room temperature (15-30° C., similarly hereinafter). Diisopropyl azodicarboxylate is added dropwise to the solution under the protection of nitrogen. The resulting mixture is then stirred at a temperature from room temperature to 40° C. to react for a period, e.g. 18 hours. After the completion of the reaction, post-processing steps can be as follows: the reaction mixture is cooled to room temperature and filtered by suction to obtain a product; if no solid separates out during the cooling, the reaction solution is concentrated under a reduced pressure to dryness, and separated by a silica gel column chromatography to obtain a product.

In another preferable embodiment, the method of preparing the compound of formula (I) or a pharmaceutically acceptable salt thereof, comprises reacting the compound of formula (III) with the compound of formula (IV) in presence of a solvent, a base, an optional catalyst, and an optional surfactant.

For instance, the base can be 1,8-diazabicyclo(5.4.0)-undec-7-ene (DBU):

For instance, the compound of formula (III) (core structure), the compound of formula (IV) (side chain) and 1,8-diazabicyclo(5.4.0)-undec-7-ene (DBU) are dissolved in a solvent such as ethanol or N-methyl pyrrolidone (surfactant such as tetrabutylammonium bromide is needed). The reaction mixture is heated to a temperature such as 85° C. and stirred for 24 to 48 hours to conduct the reaction. Post-processing steps can be as follows. In case that the solvent is ethanol, the reaction mixture can be directly concentrated to produce a crude product. In case that the solvent is N-methyl pyrrolidone, the reaction mixture is cooled to room temperature, poured into water, and extracted (e.g. with ethyl acetate). The resulting organic layers are combined, washed (e.g. with a saturated NaCl solution), dried (e.g. over anhydrous sodium sulfate) and filtered. The filtrate is concentrated under a reduced pressure to dryness to obtain a crude product. The crude product is separated by a column chromatography, and then purified by a preparative thin layer chromatography to produce a final product.

The base can also be cesium carbonate:

For instance, the compound of formula (III) (core structure), the compound of formula (IV) (side chain), cesium carbonate and a catalyst such as cuprous iodide are dissolved in a solvent such as N,N-dimethylformamide (DMF). The resulting mixture is then heated to a temperature such as 120° C. and stirred for a period e.g., 18 hours to conduct the reaction. Post-processing steps can be as follows. The reaction mixture is cooled to room temperature, poured into water, and extracted (e.g. with ethyl acetate). The resulting organic layers are combined, dried (e.g. over anhydrous sodium sulfate) and filtered by suction. The filtrate is concentrated under a reduced pressure to dryness to obtain a crude product. The crude product is purified by a preparative thin layer chromatography to produce a final product.

The base can also be $K_2CO_3$:

For instance, the compound of formula (III) (core structure), the compound of formula (IV) (side chain), and $K_2CO_3$ are dissolved in a solvent such as N,N-dimethylformamide (DMF) or acetonitrile. The resulting mixture is heated to a temperature from 60° C. to 120° C. and stirred for 2 to 18 hours. Post-processing steps can be as follows: the reaction mixture was cooled to room temperature and poured into water, and extracted (with e.g. ethyl acetate). The organic layer was combined, dried (e.g. over anhydrous sodium sulfate) and filtered by suction. The filtrate is concentrated under a reduced pressure to dryness to obtain a crude product. The crude product is purified by a silica gel column chromatography to produce a final product.

In a preferable embodiment, the present compounds can be produced from the compound of formula (II), which is an intermediate that can be obtained from the compound of formula (III). The compound of formula (II), the side chain compound such as a primary or secondary amine compound, $HNR^eR^f$, wherein $R^e$ and $R^f$ are defined as above, preferably a secondary amine compound (e.g., dimethylamine hydrochloride or tetrahydropyrrole) and $K_2CO_3$ are dissolved in a solvent such as acetonitrile. The resulting mixture is heated to a temperature from 60° C. to 120° C. and stirred for 2 to 18 hours. Post-processing steps can be as follows. The reaction mixture is concentrated, and water is added. The resulting solution is extracted (e.g. with dichloromethane). The combined organic phases are dried (e.g. over anhydrous sodium sulfate), and concentrated to obtain a crude product. The crude product is purified by a silica gel column chromatography to produce a final product.

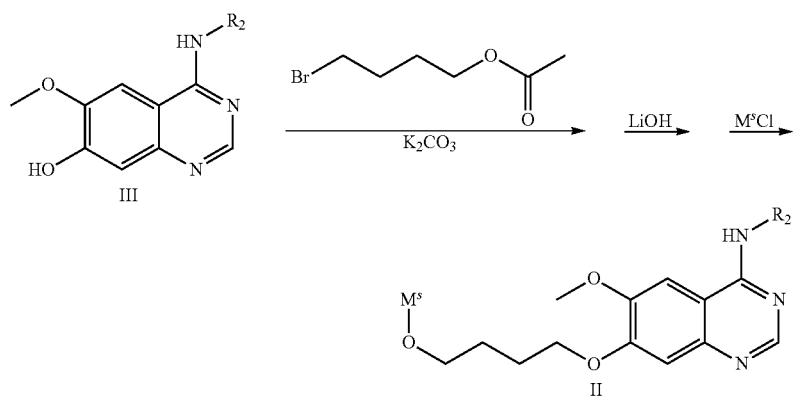

The preparation of formula (II) is as follows:

Step 1

The compound of formula (III) is dissolved in a solvent such as N,N-dimethylformamide (DMF). $K_2CO_3$ and 4-bromobutyl acetate are added at room temperature. The resulting mixture is reacted at a temperature such as 50° C. for a period e.g., 2 hours. The reaction mixture is cooled to room temperature, poured into water, and extracted (e.g. with dichloromethane). The organic layers are combined, dried (e.g. over anhydrous sodium sulfate), concentrated under a reduced pressure to dryness to obtain a crude product (as a yellow oil). The crude product is used directly in the next step.

Step 2

The product of step 1 is dispersed in methanol, and water and lithium hydroxide are added. The resulting mixture is reacted at room temperature overnight. The reaction mixture is concentrated under a reduced pressure to dryness. Water and ethyl acetate are added. Upon stirring the resulting mixture, a solid separates out and is filtered by suction. The filter cake is dried to produce a product, which is directly used in the next step.

Step 3

The product of step 2 is dispersed in dichloromethane, and triethylamine is added. Then methylsulfonyl chloride is added dropwise under an ice-bath. After the dropwise addition, the resulting mixture is reacted for 3 hours at room temperature. Water is added, and the resulting solution is extracted with dichloromethane. The combined organic layer is dried (e.g. over anhydrous sodium sulfate), and concentrated under a reduced pressure to dryness to obtain a product.

EXAMPLES

The abbreviations in the examples have the following meanings:
THF Tetrahydrofuran
DMF N,N-dimethylformamide
DBU 1,8-diazabicyclo(5.4.0)-undec-7-ene
DIPEA N,N-diisopropylethylamine
DBN 1,5-diazabicyclo[4.3.0]non-5-ene
DCC N,N'-dicyclohexylcarbodiimide
EDC 1-(3-dimethylaminopropyl)-3-ethyl-carbodiimide
DIC N,N'-diisopropylcarbodiimide
DIAD diisopropyl azodicarboxylate
DCM methylene chloride
EDCl or EDCl.HCl 1-(3-dimethylaminopropyl)-3-ethylcarbodiimide hydrochloride
HOBT 1-hydroxybenzotrizole

PREPARATION EXAMPLES

In the following examples, 4-(4-bromo-2-fluoroanilino)-6-methoxy-7-hydroxyquinazoline and its trifluoroacetic acid salt (Formula (III)-1, core structure 1 and its trifluoroacetic acid salt) can be prepared in a manner similar to the preparation of core structure 2 and its trifluoroacetic acid salt, and they can also be purchased from NANJING CHICO. Other raw materials are commercially available or prepared in lab. The methods of preparation are described as follows.

4-(3-chloro-4-fluoroanilino)-6-methoxy-7-hydroxyquinazoline or its trifluoroacetic acid salt (Formula (III)-2, core structure 2 and its trifluoroacetic acid salt) can be prepared in lab by the following method:

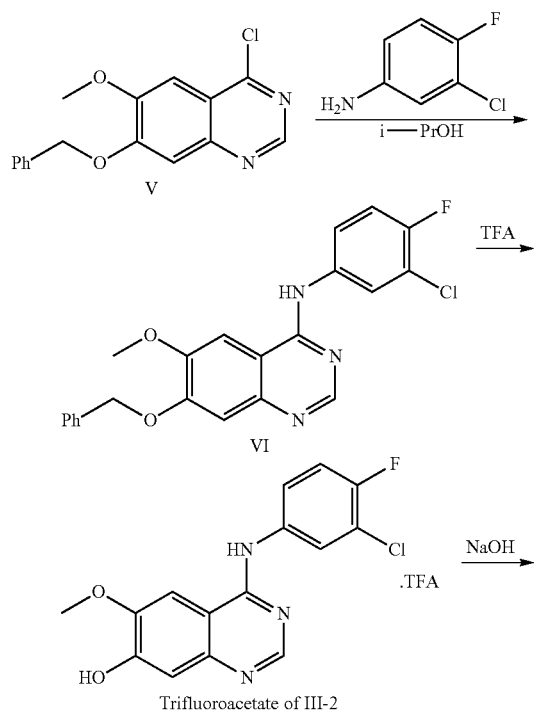

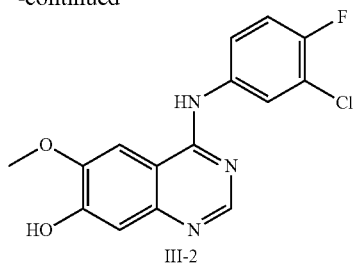

Step 1

4-chloro-6-methoxy-7-benzyloxyquinazoline (formula V, 30.0 g, 99.8 mmol) and 3-chloro-4-fluoroaniline (17.4 g, 119.7 mmol) were dispersed in isopropyl alcohol (600 mL) at room temperature. The resulting dispersion was heated to reflux for 18 hours to conduct the reaction. The reaction mixture was cooled to room temperature, filtered under a reduced pressure, and dried to produce an off-white solid (36.0 g), i.e., 4-(3-chloro-4-fluoroanilino)-6-methoxy-7-benzyloxyquinazoline (formula VI).

Step 2

The compound of formula VI (36.0 g), obtained from step 1, was dissolved in trifluoroacetic acid (300 mL), and the mixture was heated to 70° C. and stirred for 18 hours. The resulting mixture was concentrated to dryness to obtain a crude product of trifluoroacetate of III-2. The crude product was added to methyl tert-butyl ether to form a slurry. The slurry was then filtered and dried to obtain a off-white solid (29.7 g), which is trifluoroacetate of III-2 (The total yield for two steps: 69%).

Step 3

Purified water (200 mL) was added to the solid (23.0 g) of trifluoroacetate of III-2 obtained in the previous step to form a slurry. Under being stirred, to the slurry was added dropwise an aqueous solution of 1N NaOH to adjust the pH to 8. The resulting mixture was extracted with ethyl acetate. The organic layer was dried over anhydrous Na$_2$SO$_4$, and concentrated to produce 15.7 g of an off-white solid, i.e., core structure 111-2, yield: 93%.

Synthesis of 4-chloro-N,N-dimethylbutan-1-amine hydrochloride 4-hydroxy-N,N-dimethylbutylamine (1.0 g, 8.53 mmol) was added dropwise to thionyl chloride (5 mL) in an ice-water bath, and the environment was kept below 10° C. in the dropwise addition. After the completion of the dropwise addition, the mixture was warmed naturally to room temperature, and then stirred for 12 hours at room temperature. The reaction mixture was added dropwise to ethanol (100 mL) that was cooled previously to 0-5° C. The resulting mixture was concentrated to produce the title compound as a white solid (1.3 g, yield: 89%).

Synthesis of N-hydroxybutylpyrrolidine 4-chloro-n-butanol (5.0 g, 46.1 mmol), tetrahydropyrrole (6.6 g, 92.6 mmol) and potassium carbonate (12.7 g, 92.6 mmol) were added to acetonitrile (150 mL) at room temperature, and the mixture was stirred for 18 hours at 80° C. Then the reaction mixture was cooled to room temperature and filtered. The filtrate was concentrated to produce a brown oil (6.8 g), which was directly used in the next step.

Synthesis of N-methyl-6-bromo-hexanamide 6-bromo-n-hexanoic acid (9.5 g, 50 mmol) and N,N-dimethylformamide (DMF, 5 mL) were dissolved in methylene chloride (DCM, 150 mL) at room temperature. To the resulting mixture was added slowly and dropwise oxalyl chloride (12.6 g, 100 mmol). After the completion of dropwise addition, the mixture was stirred for 1 hour at room temperature to conduct the reaction. The reaction mixture was concentrated, and the residue was dissolved in methylene chloride (DCM, 100 mL). The resulting mixture was added to a reaction vessel containing a solution of methylamine in ethanol (50 mL). The mixture was stirred for 2 hours at room temperature to conduct the reaction, and then methylene chloride (DCM, 500 mL) was added. Then the resulting mixture was washed with 1N hydrochloric acid (500 mL), a saturated aqueous NaHCO$_3$ solution (500 mL) and a saturated brine (500 mL) successively, dried over anhydrous Na$_2$SO$_4$, and concentrated to produce a white solid (4.0 g), which was directly used in the next step.

Synthesis of N,N-dimethyl-6-bromo-hexanamide 6-bromohexanoic acid (1.94 g, 10 mmol), methylamine hydrochloride (1.21 g, 15 mmol), triethylamine (2 g, 20 mmol), 1-(3-dimethylaminopropyl)-3-ethyl-carbodiimide hydrochloride (EDCl, 2.11 g, 11 mmol) and 1-hydroxybenzotriazole (HOBT, 0.5 g) were dissolved in methylene chloride (DCM, 150 mL). The mixture was stirred for 3 hours at 15° C. to conduct the reaction, and methylene chloride (DCM, 150 mL) was added to the reaction system. The resulting mixture was washed with 1N diluted hydrochloric acid (150 mL), a saturated aqueous NaHCO$_3$ solution (150 mL), and a saturated brine (150 mL) successively, dried over anhydrous sodium sulfate and concentrated to produce a colorless oil (2.0 g), which was directly used in the next step.

Synthesis of 5-bromopentanamide 5-bromopentanoic acid (5 g, 27.6 mmol) was dissolved in methylene chloride (50 mL). To the resulting solution was added N,N-dimethylformamide (DMF). The resulting mixture was cooled to 0-5° C. in an ice-water bath. To the cooled mixture was slowly and dropwise added oxalyl chloride (10 g, 82.8 mmoL). After the completion of the dropwise addition, the mixture was stirred for 2 hours at 40° C. to conduct the reaction. The reaction mixture was concentrated under a reduced pressure to produce a yellow solid. The resulting solid was dissolved in tetrahydrofuran (THF, 50 mL). The resulting solution was slowly and dropwise added to ammonia-water (10 mL). The resulting mixture was stirred for 2 hours at room temperature, and extracted with methylene chloride. The organic phase was dried over anhydrous sodium sulfate and concentrated to produce a white solid (4.85 g, yield: 98%).

Synthesis of 4-chlorobutanamide

Step 1

At room temperature, 4-chlorobutanoic acid (20 g, 164 mmol) was dissolved in methylene chloride (200 mL). The resulting solution was cooled to 0-5° C. To the cooled solution was added dropwise oxalyl chloride (41 g, 328 mmoL). After the completion of the dropwise addition, the resulting mixture was stirred for 2 hours at room temperature, and concentrated to produce a crude product of 4-chlorobutanoyl chloride (22 g), which was directly used in the next step.

Step 2

To a solution of ammonia-water (20 mL) in tetrahydrofuran (THF, 100 mL), which was cooled to 0-5° C. in an ice-bath, was dropwise added a solution of 4-chlorobutanoyl chloride (22 g) in tetrahydrofuran (THF, 100 mL). After the completion of dropwise addition, the mixture was reacted for 1 hour at temperature. The reaction mixture was poured into water (1 L). The resulting mixture was extracted with ethyl acetate. The organic layer was dried over anhydrous sodium sulfate and concentrated under a reduced pressure to produce a white solid (7 g, yield: 35%).

Synthesis of 3-(1H-imidazol-1-yl)propan-1-ol

At room temperature, 3-bromopropan-1-ol (10 g, 72.4 mmol), imidazole (4.92 g, 72.4 mmol) and K$_2$CO$_3$ (25 g, 181 mmol) were dispersed in acetonitrile (150 mL). The resulting mixture was heated to reflux for and stirred 18 hours, and then cooled to room temperature. The cooled mixture was poured into water (1 L). The resulting mixture was extracted with ethyl acetate. The organic layer was dried over anhydrous sodium sulfate, and concentrated under a reduced pressure to produce a colorless oil (4 g).

Synthesis of 2-methyl-5-bromomethylthiazole

Step 1: Synthesis of
2-methyl-5-hydroxymethylthiazole

At room temperature, lithium aluminum hydride (8.88 g, 234 mmol) was dispersed in anhydrous tetrahydrofuran (THF, 100 mL). The resulting mixture was cooled to 0-5° C. in an ice-water bath. To the cooled mixture was dropwise added a solution of 2-methyl-5-ethoxyformylthiazole (20 g, 117 mmol) in anhydrous tetrahydrofuran (THF, 100 mL). After the completion of the dropwise addition, the reaction mixture was naturally warmed to room temperature, and was stirred for 18 hours at room temperature. To the reaction mixture was dropwise added water (10 mL) at 0-5° C. After the completion of the dropwise addition, the resulting mixture was filtered. The filtrate was concentrated to produce a yellow oily substance (12 g), which was directly used in the next step.

Step 2: Synthesis of
2-methyl-5-bromomethylthiazole

At room temperature, 2-methyl-5-hydroxymethylthiazole (12 g) was dissolved in methylene chloride (500 mL), and the resulting solution was cooled to 0-5° C. in an ice-water bath. To the cooled mixture were added successively and in batches triphenylphosphine (52 g, 200 mmol) and carbon tetrabromide (66 g, 200 mmol). After the completion of the addition, the reaction mixture was naturally warmed to room temperature, stirred for 2 hours at room temperature, concentrated, and purified by a silica gel column chromatography (petroleum ether:ethyl acetate=2:1) to produce a yellow solid (3.3 g, the total yield for two steps: 15%).

Synthesis of 2-methyl-4-chloromethylthiazole

Thioacetamide (2 g, 26.6 mmol) and dichloroacetone (4.05 g, 31.9 mmol) were dissolved in ethanol (60 mL) at room temperature. The resulting solution was heated to 80° C. and reacted for 4 hours. After the completion of the reaction, the reaction mixture was concentrated. To the residue was added 100 mL of purified water. The resulting mixture was adjusted with sodium bicarbonate to a pH of 8. The mixture was extracted with methyl tert-butyl ether, and the organic layer was dried over anhydrous sodium sulfate, and concentrated to obtain a product (1.2 g).

Synthesis of 1-(2-chloroethyl)-1H-imidazole

Potassium hydroxide (11.2 g), potassium carbonate (8.84 g) and tetrabutyl ammonium bromide (0.21 g) were placed in a three-necked flask at room temperature. To the mixture was added 1,2-dichloroethane (80 mL) while stirring the mixture. The resulting mixture was warmed to 50° C. Then imidazole (2.04 g) was added. The mixture was reacted for 2 hours at 50° C. After the completion of the reaction, the reaction mixture was cooled to room temperature and filtered. The organic layer was dried over anhydrous sodium sulfate and concentrated to produce an oily substance (1.45 g).

Synthesis of 2-methyl-4-methylsulfonyloxyethylthiazole

Step 1: Synthesis of ethyl 2-(2-methylthiazol-4-yl) acetate

Ethyl chloroacetoacetate (5.0 g, 30.5 mmol) and thioacetamide (2.3 g, 30.5 mmol) were dissolved in anhydrous ethanol (50 mL) at room temperature. The mixture was heated to reflux for 24 hours and concentrated to produce a crude product. The crude product was purified by a silica gel column chromatography (petroleum ether:ethyl acetate=1:1) to produce a white waxy solid (3.0 g, yield: 53%).

Step 2: Synthesis of 2-methyl-4-hydroxyethylthiazole

At room temperature, lithium aluminum hydride (1.2 g, 32.4 mmol) was dispersed in anhydrous tetrahydrofuran (THF, 20 mL). The mixture was cooled to 0-5° C. in an ice-water bath. To the cooled mixture was dropwise added a solution of ethyl 2-(2-methylthiazol-4-yl) acetate (3.0 g, 16.2 mmol) in anhydrous tetrahydrofuran (THF, 10 mL). After the completion of the dropwise addition, the reaction mixture was naturally warmed to room temperature, stirred for 18 hours at room temperature, and then cooled to 0-5° C. To the cooled mixture was dropwise added water (1.5 mL) to quench the reaction. After the completion of the dropwise addition, the resulting mixture was filtered by suction. The filtrate was concentrated to produce a yellow oily liquid (1.6 g), which was directly used in the next step.

Step 3: Synthesis of 2-methyl-4-methylsulfonyloxyethylthiazole 2-methyl-4-hydroxyethylthiazole (1.6 g, 11.2 mmol) and triethylamine (2.3 g, 22.4 mmol) were dissolved in methylene chloride (20 mL). The mixture was cooled to 0-5° C. To the cooled mixture was added methanesulfonyl chloride (1.9 g, 16.8 mmol). After the completion of the dropwise addition, the resulting mixture was naturally cooled to room temperature, stirred for 1 hour at room temperature and poured into water (100 mL). Then the resulting mixture was extracted with methylene chloride, and the organic layer was dried over anhydrous sodium sulfate, and concentrated under a reduced pressure to produce a yellow waxy solid (2.0 g).

Example 1

Synthesis of 4-(4-bromo-2-fluoroanilino)-6-methoxy-7-((1,3-benzodioxole-5-yl)methoxy)quinazoline (Compound 1)

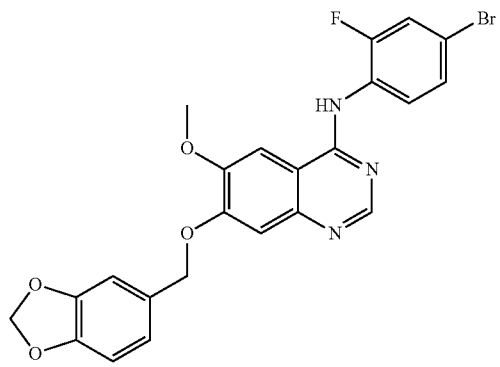 [SMILES: COc1cc2c(Nc3ccc(Br)cc3F)ncnc2cc1OCc1ccc2c(c1)OCO2]

4-(4-bromo-2-fluoroanilino)-6-methoxy-7-hydroxyquinazoline trifluoroacetic acid salt (400 mg, 0.84 mmol), 5-bromomethylbenzo[d][1,3]dioxole (181 mg, 0.84 mmol) and potassium carbonate (289 mg, 2.09 mmol) were dispersed in N,N-dimethylformamide (DMF, 5 mL). The mixture was stirred for 18 hours at 60° C. while maintaining the constant temperature and then cooled to room temperature. The cooled mixture was poured into water (100 mL). The resulting mixture was extracted with ethyl acetate. The organic layer was dried over anhydrous sodium sulfate, and concentrated under a reduced pressure to obtain a crude product. The crude product was purified by a silica gel column chromatography (petroleum ether:ethyl acetate=1:1) to produce an off-white solid (115 mg, yield: 27%).

$^1$H-NMR (400 MHz, DMSO-d6) δ: 9.54 (s, 1H), 8.35 (s, 1H), 7.81 (s, 1H), 7.66 (dd, 1H, J=9.8, 1.8 Hz), 7.53 (t, 1H, J=8.2 Hz), 7.49-7.43 (m, 1H), 7.29 (s, 1H), 7.06 (s, 1H), 6.99 (d, 1H, J=8.0 Hz), 6.95 (d, 1H, J=7.6 Hz), 6.04 (s, 2H), 5.17 (s, 2H), 3.94 (s, 3H).

MS: m/z 498, 500 (M+1).

Example 2

Synthesis of 4-(4-bromo-2-fluoroanilino)-6-methoxy-7-((2-pyrrolidine-1-yl)ethoxy)quinazoline (Compound 21

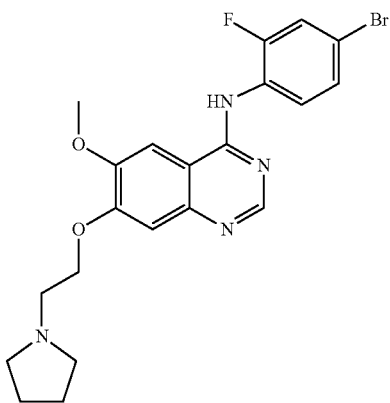 [SMILES: COc1cc2c(Nc3ccc(Br)cc3F)ncnc2cc1OCCN1CCCC1]

4-(4-bromo-2-fluoroanilino)-6-methoxy-7-hydroxyquinazoline trifluoroacetic acid salt (200 mg, 0.42 mmol), N-chloroethylpyrrolidine hydrochloride (71 mg, 0.42 mmol), and potassium carbonate (232 mg, 1.68 mmol) were dispersed in N,N-dimethylformamide (DMF, 10 mL). The mixture was stirred for 5 hours while being maintained at 60° C. and then cooled to room temperature. The cooled mixture was poured into water (75 mL). The resulting mixture was extracted with ethyl acetate. The organic layer was dried over anhydrous sodium sulfate, and concentrated under a reduced pressure to produce a crude product (300 mg). The crude product was purified by a preparative thin-layer chromatography (methylene chloride:methanol=10:1) to produce a light yellow solid (120 mg, yield: 62%).

$^1$H-NMR (400 MHz, CDCl$_3$) δ: 8.66 (s, 1H), 8.41 (t, 1H, J=8.4 Hz), 7.59-7.47 (br s, 1H), 7.38-7.32 (m, 2H), 7.25 (s, 1H), 7.11 (s, 1H), 4.57-4.50 (m, 2H), 4.01 (s, 3H), 3.41-3.33 (m, 2H), 3.27-3.07 (m, 4H), 2.09-1.96 (m, 4H).

MS 231, 232 (½M+1).

Example 3

Synthesis of 4-(4-bromo-2-fluoroanilino)-6-methoxy-7-(3-cyanobenzyloxy) quinazoline (Compound 3)

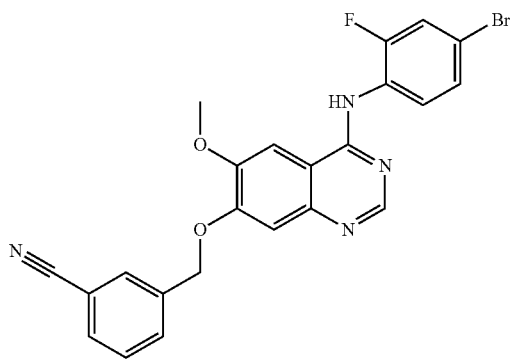 [SMILES: COc1cc2c(Nc3ccc(Br)cc3F)ncnc2cc1OCc1cccc(C#N)c1]

4-(4-bromo-2-fluoroanilino)-6-methoxy-7-hydroxyquinazoline trifluoroacetic acid salt (300 mg, 0.63 mmol), 3-(bromomethyl)benzonitrile (147 mg, 0.75 mmol), and potassium carbonate (261 mg, 1.89 mmol) were dispersed in acetonitrile (10 mL) at room temperature. The mixture was heated to reflux for and stirred 2 hours. The reaction mixture was cooled to room temperature and poured into water (100 mL). The resulting mixture was extracted with ethyl acetate. The organic layer was dried over anhydrous sodium sulfate, and concentrated under a reduced pressure to obtain a crude product. The crude product was purified by a preparative thin-layer chromatography (methylene chloride:methanol=10:1) to produce a white solid (120 mg, yield: 40%).

$^1$H-NMR (400 MHz, DMSO-d6) δ: 9.61 (s, 1H), 8.37 (s, 1H), 7.97 (s, 1H), 7.91-7.82 (m, 3H), 7.72-7.62 (m, 2H), 7.58-7.44 (m, 2H), 7.32 (s, 1H), 5.37 (s, 2H), 3.96 (s, 3H).

MS 479, 481 (M+1).

Example 4

Synthesis of 4-(4-bromo-2-fluoroanilino)-6-methoxy-7-(4-trifluoromethyl-benzyloxy)quinazoline (Compound 5)

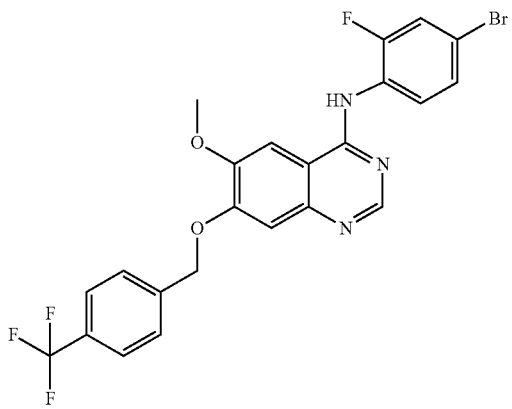 [SMILES: COc1cc2c(Nc3ccc(Br)cc3F)ncnc2cc1OCc1ccc(C(F)(F)F)cc1]

4-(4-bromo-2-fluoroanilino)-6-methoxy-7-hydroxyquinazoline (500 mg, 1.37 mmol), 1-(trifluoromethyl)-4-bromomethylbenzene (393 mg, 1.64 mmol) and potassium carbonate (568 mg, 4.11 mmol) were dispersed in N,N-dimethylformamide (DMF, 15 mL). The resulting mixture was heated to reflux for 4 hours to conduct the reaction. The reaction mixture was cooled to room temperature and poured into water (80 mL). The resulting mixture was extracted with ethyl acetate. The organic layer was dried over anhydrous sodium sulfate, and concentrated to obtain a crude product (800 mg). The crude product was purified by a preparative thin-layer chromatography (methylene chloride:methanol=10:1) to produce a white solid (287 mg, yield: 40%).

$^1$H-NMR (400 MHz, DMSO-d6) δ: 9.57 (s, 1H), 8.36 (s, 1H), 7.85-7.80 (m, 3H), 7.74-7.72 (m, 2H), 7.66 (dd, 1H, =10.0, 2.0 Hz), 7.53-7.45 (m, 2H), 7.30 (s, 1H), 5.43 (s, 2H), 3.97 (s, 3H).

MS 522, 524 (M+1).

Example 5

Synthesis of 6-(4-(4-bromo-2-fluoroanilino)-6-methoxyquinazolin-7-yl-oxy)hexanamide (Compound 6)

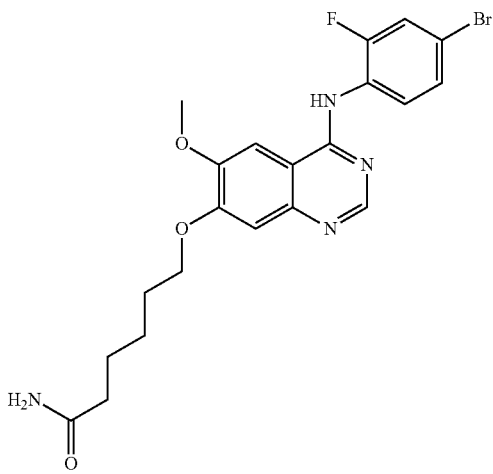 [SMILES: COc1cc2c(Nc3ccc(Br)cc3F)ncnc2cc1OCCCCCC(N)=O]

4-(4-bromo-2-fluoroanilino)-6-methoxy-7-hydroxyquinazoline trifluoroacetic acid salt (400 mg, 0.84 mmol), 6-bromohexanamide (326 mg, 1.68 mmol) and potassium carbonate (232 mg, 1.68 mmol) were dispersed in acetonitrile (10 mL). The mixture was stirred for 18 hours at 80° C. while maintaining the constant temperature. The reaction mixture was cooled to room temperature and poured into water (75 mL). A solid separated out. The resulting mixture was filtered and dried to produce an off-white solid (170 mg, yield: 42%).

$^1$H-NMR (400 MHz, DMSO-d6) δ: 9.53 (s, 1H), 8.35 (s, 1H), 7.79 (s, 1H), 7.66 (dd, 1H, J=10.0, 2.0 Hz), 7.53 (t, 1H, J=8.2 Hz), 7.46 (dd, 1H, J=8.4, 1.6 Hz) 7.25 (br s, 1H), 7.18 (s, 1H), 6.70 (br s, 1H), 4.13 (t, 2H, J=6.6 Hz), 3.94 (s, 3H), 2.80 (t, 2H, J=7.2 Hz), 1.85-1.75 (m, 2H), 1.63-1.52 (m, 2H), 1.49-1.39 (m, 2H).

MS 477, 479 (M+1).

Example 6

Synthesis of 4-(4-bromo-2-fluoroanilino)-6-methoxy-7-((6-methylpyridine-2-yl)methoxy)quinazoline (Compound 7)

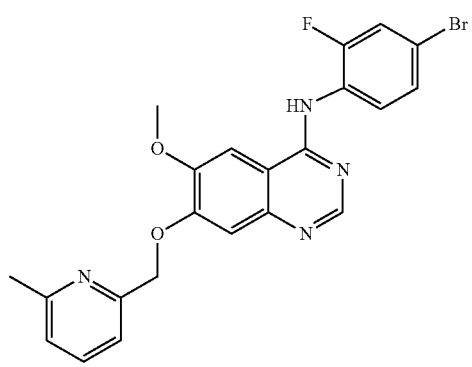 [SMILES: COc1cc2c(Nc3ccc(Br)cc3F)ncnc2cc1OCc1cccc(C)n1]

4-(4-bromo-2-fluoroanilino)-6-methoxy-7-hydroxyquinazoline trifluoroacetic acid salt (400 mg, 0.84 mmol), 6-methyl-2-hydroxymethylpyridine (103 mg, 0.84 mmol) and potassium carbonate (289 mg, 2.09 mmol) were dispersed in N, N-dimethylformamide (DMF, 5 mL) at room temperature. The mixture was stirred for 18 hours at 60° C. while maintaining the constant temperature. The reaction mixture was cooled to room temperature and poured into water (100 mL). The resulting mixture was extracted with ethyl acetate. The organic layer was dried over anhydrous sodium sulfate, and concentrated under a reduced pressure to obtain a crude product. The crude product was purified by a silica gel column chromatography (methylene chloride: methanol=50:1) to produce a light brown solid (215 mg, yield: 55%).

$^1$H-NMR (400 MHz, DMSO-d6) δ: 9.55 (s, 1H), 8.35 (s, 1H), 7.84 (s, 1H), 7.74 (t, 1H, J=8.0 Hz), 7.70-7.62 (m, 1H), 7.58-7.42 (m, 2H), 7.35 (d, 1H, J=7.6 Hz), 7.30-7.20 (m, 2H), 5.30 (s, 2H), 3.97 (s, 3H), 2.50 (s, 3H).

MS 469, 471 (M+1).

Example 7

Synthesis of 4-(4-bromo-2-fluoroanilino)-6-methoxy-7-(2-(2-methyl-1H-benzo[d]imidazole-1-yl)ethoxy)quinazoline (Compound 8)

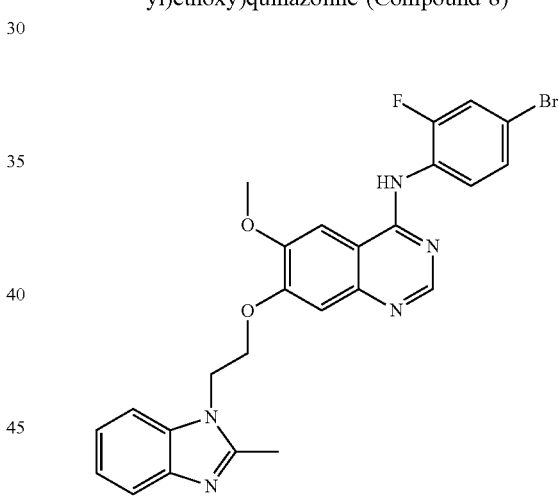

4-(4-bromo-2-fluoroanilino)-6-methoxy-7-hydroxyquinazoline (200 mg, 0.55 mmol), 2-(2-methyl-1H-benzo[d]imidazol-1-yl)ethanol (97 mg, 0.55 mmol), triphenylphosphine (172 mg, 0.65 mmol) and diisopropyl azodicarboxylate (DIAD, 131 mg, 0.65 mmol) were dissolved in anhydrous tetrahydrofuran (THF, 5 mg). The resulting mixture was stirred for 18 hours at 40° C. under the protection of nitrogen to conduct the reaction. The reaction mixture was cooled to room temperature. A solid separated out. The mixture was filtered and dried to produce an off-white solid (249 mg, yield: 87%).

$^1$H-NMR (400 MHz, DMSO-d6) δ: 9.52 (s, 1H), 8.34 (s, 1H), 7.77 (s, 1H), 7.66-7.62 (m, 2H), 7.54-7.44 (m, 3H), 7.22-7.12 (m, 3H), 4.69 (t, 2H, J=4.6 Hz), 4.47 (t, 2H, J=4.8 Hz), 3.91 (s, 3H), 2.70 (s, 3H).

MS 522, 524 (M+1).

Example 8

Synthesis of 4-(4-bromo-2-fluoroanilino)-6-methoxy-7-(4-morpholinobenzyloxy)quinazoline (Compound 12)

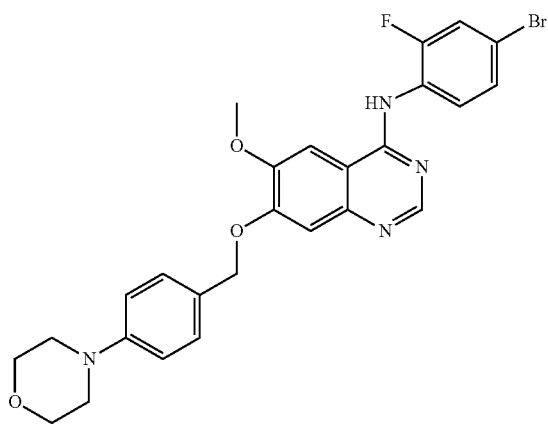 [SMILES: COc1cc2c(Nc3ccc(Br)cc3F)ncnc2cc1OCc1ccc(N2CCOCC2)cc1]

4-(4-bromo-2-fluoroanilino)-6-methoxy-7-hydroxyquinazoline (500 mg, 1.37 mmol), (4-morpholinophenyl)methanol (396 mg, 2.05 mmol), triphenylphosphine (538 mg, 2.05 mmol) and diisopropyl azodicarboxylate (DIAD, 415 mg, 2.05 mmol) were dissolved in anhydrous tetrahydrofuran (THF, 10 mL) at room temperature, and the solution was stirred for 18 hours at 40° C. under the protection of nitrogen to conduct the reaction. Then the resulting mixture was concentrated and purified by a silica gel column chromatography (methylene chloride:methanol=10:1) to produce a yellow solid (340 mg, yield: 46%).

$^1$H-NMR (400 MHz, DMSO-d6) δ: 8.50 (s, 1H), 7.86 (s, 1H), 7.51 (d, 1H, J=9.6 Hz), 7.35 (d, 1H, J=8.0 Hz), 7.20 (d, 3H, J=8.0 Hz), 6.91 (d, 3H, J=8.8 Hz) 5.26 (s, 2H), 3.87 (s, 3H), 3.70 (t, 4H, J=4.6 Hz), 3.07 (t, 4H, J=4.4 Hz).

MS 539, 541 (M+1).

Example 9

Synthesis of 4-(4-bromo-2-fluoroanilino)-6-methoxy-7-(3-(1H-imidazol-1-yl)propoxy)quinazoline (Compound 14)

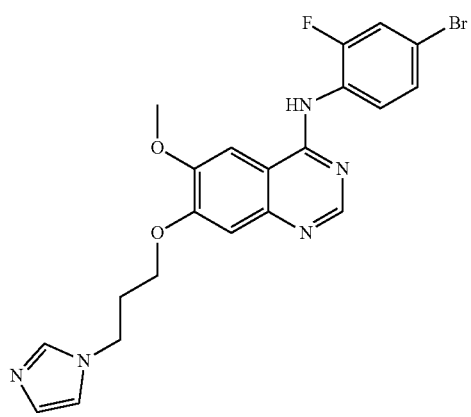 [SMILES: COc1cc2c(Nc3ccc(Br)cc3F)ncnc2cc1OCCCn1ccnc1]

4-(4-bromo-2-fluoroanilino)-6-methoxy-7-hydroxyquinazoline trifluoroacetic acid salt (400 mg, 0.84 mmol), 3-(1H-imidazol-1-yl)propan-1-ol (400 mg, 3.17 mmol), triphenylphosphine (330 mg, 1.26 mmol) and diisopropyl azodicarboxylate (DIAD, 255 mg, 1.26 mmol) were dissolved in anhydrous tetrahydrofuran (THF, 10 mL) at room temperature. The resulting mixture was stirred for 18 hours at room temperature under the protection of nitrogen, and dried by evaporation obtain a crude product. The crude product was re-crystallized subjected to with methanol/ethyl acetate (v/v=1:1) to produce a light yellow solid (220 mg, yield: 55%).

$^1$H-NMR (400 MHz, DMSO-d6) δ: 9.56 (s, 1H), 8.35 (s, 1H), 7.82 (s, 1H), 7.70-7.62 (m, 2H), 7.56-7.44 (m, 2H), 7.25-7.15 (m, 2H), 6.90 (s, 1H), 4.17 (t, 2H, J=7.0 Hz), 4.09 (t, 2H, J=6.6 Hz), 3.96 (s, 3H), 2.31-2.21 (m, 2H).

MS 472, 474 (M+1).

Example 10

Synthesis of 4-(4-bromo-2-fluoroanilino)-6-methoxy-7-((tetrahydropyran-4-yl)methoxy)quinazoline (Compound 15)

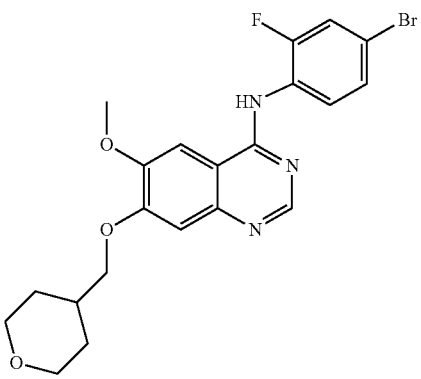 [SMILES: COc1cc2c(Nc3ccc(Br)cc3F)ncnc2cc1OCC1CCOCC1]

4-(4-bromo-2-fluoroanilino)-6-methoxy-7-hydroxyquinazoline trifluoroacetic acid salt (400 mg, 0.84 mmol), 4-iodomethyltetrahydropyran (190 mg, 0.84 mmol) and potassium carbonate (289 mg, 2.09 mmol) were dispersed in N,N-dimethylformamide (DMF, 5 mL). The mixture was stirred for 15 hours at 60° C. to conduct the reaction. The resulting reaction mixture was cooled to room temperature and poured into water (100 mL). The resulting mixture was extracted with ethyl acetate. The organic layer was dried over anhydrous sodium sulfate, and concentrated under a reduced pressure to obtain a crude product. The crude product was purified by a silica gel column chromatography (methylene chloride:methanol=50:1) to produce a white solid (170 mg, yield: 44%).

$^1$H-NMR (400 MHz, DMSO-d6) δ: 9.53 (s, 1H), 8.35 (s, 1H), 7.80 (s, 1H), 7.66 (dd, 1H, J=9.8, 2.0 Hz), 7.53 (t, 1H, J=8.4 Hz), 7.47 (dd, 1H, J=8.4, 1.6 Hz), 7.20 (s, 1H), 4.02 (d, 2H, J=6.4 Hz), 3.95 (s, 3H), 3.89 (dd, 2H, J=11.4, 3.0 Hz), 3.41-3.33 (m, 2H), 2.16-2.03 (m, 1H), 1.76-1.66 (m, 2H), 1.45-1.32 (m, 2H).

MS 462, 464 (M+1).

Example 11

Synthesis of 4-(4-bromo-2-fluoroanilino)-6-methoxy-7-((2-methylthiazole-4-yl)methoxy)quinazoline (Compound 17)

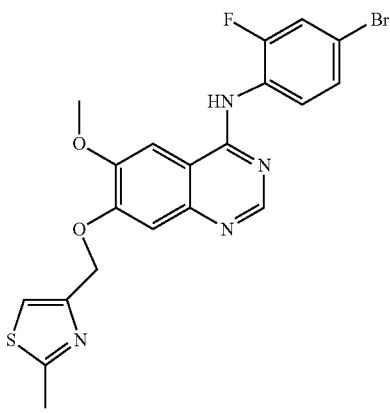 [SMILES: COc1cc2c(Nc3ccc(Br)cc3F)ncnc2cc1OCc1csc(C)n1]

4-(4-bromo-2-fluoroanilino)-6-methoxy-7-hydroxyquinazoline trifluoroacetic acid salt (500 mg, 1.05 mmol), 2-methyl-4-chloromethylthiazole (185 mg, 1.26 mmol), and potassium carbonate (363 mg, 2.63 mmol) were dispersed in N,N-dimethylformamide (DMF, 10 mL). The mixture was heated at 60° C. and stirred for 18 hours. The resulting reaction mixture was cooled to room temperature and poured into water (75 mL). A solid separated out. The resulting mixture was filtered and dried to produce a yellow solid (165 mg, yield: 33%).

$^1$H-NMR (400 MHz, DMSO-d6) δ: 9.56 (s, 1H), 8.37 (s, 1H), 7.82 (s, 1H), 7.70-7.63 (m, 2H), 7.54 (t, 1H, J=8.2 Hz), 7.48 (dd, 1H, J=8.4, 2.0 Hz), 7.38 (s, 1H), 5.28 (s, 2H), 3.94 (s, 3H), 2.69 (s, 3H).

MS 475, 477 (M+1).

Example 12

Synthesis of (6-(4-(4-bromo-2-fluoroanilino)-6-methoxyquinazolin-7-yl-oxy)pyridine-3-yl)(morpholino)methanone (Compound 18)

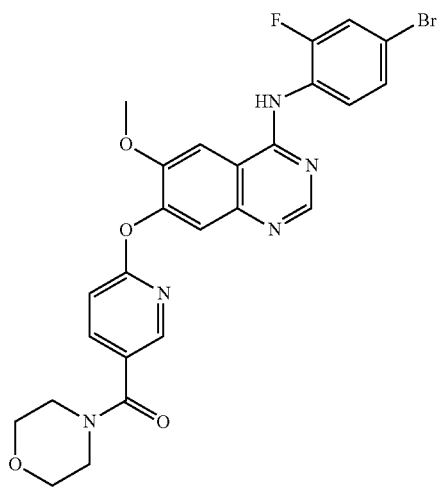 [SMILES: COc1cc2c(Nc3ccc(Br)cc3F)ncnc2cc1Oc1ccc(C(=O)N2CCOCC2)cn1]

4-(4-bromo-2-fluoroanilino)-6-methoxy-7-hydroxyquinazoline (500 mg, 1.37 mmol), (2-chloropyridin-5-yl)-(morpholino)methanone (373 mg, 1.64 mmol), cesium carbonate (1.12 g, 3.43 mmol) and cuprous iodide (19 mg, 0.1 mmol) were dispersed in N,N-dimethylformamide (DMF, 10 mL). The mixture was stirred for 18 hours at 120° C. to conduct the reaction. The reaction mixture was cooled to room temperature and poured into water (75 mL). The resulting mixture was extracted with ethyl acetate. The organic layer was dried over anhydrous sodium sulfate, and concentrated to obtain a crude product. The crude product was purified by a preparative thin-layer chromatography (methylene chloride:methanol=10:1) to produce a white solid (174 mg, yield: 23%).

$^1$H-NMR (400 MHz, DMSO-d6) δ: 9.77 (s, 1H), 8.43 (s, 1H), 8.18 (s, 1H), 8.03 (s, 1H), 7.96 (d, 1H, J=8.0 Hz), 7.70 (d, 1H, J=10.4 Hz), 7.57-7.52 (m, 3H), 7.21 (d, 1H, J=8.0 Hz), 3.88 (s, 3H), 3.62-3.32 (m, 8H).

MS 554, 556 (M+1).

Example 13

Synthesis of 4-(4-bromo-2-fluoroanilino)-6-methoxy-7-(3-(pyrrolidine-1-yl)propoxy)quinazoline (Compound 19)

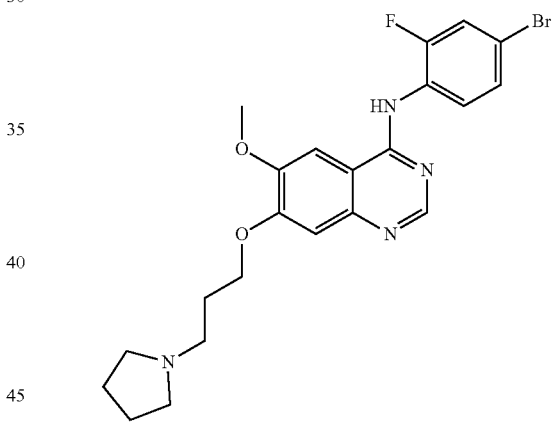

4-(4-bromo-2-fluoroanilino)-6-methoxy-7-hydroxyquinazoline trifluoroacetic acid salt (500 mg, 1.05 mmol), N-chloropropylpyrrolidine hydrochloride (193 mg, 1.05 mmol) and potassium carbonate (363 mg, 2.63 mmol) were added to N,N-dimethylformamide (DMF, 5 mL). The mixture was stirred for 18 hours at 80° C. to conduct the reaction. The reaction mixture was cooled to room temperature and poured into water (50 mL). The resulting mixture was extracted with ethyl acetate. The organic layer was dried over anhydrous sodium sulfate, and concentrated to obtain a crude product. The crude product was purified by a preparative thin-layer chromatography (methylene chloride:methanol=10:1) to produce a white solid (160 mg, yield: 32%).

$^1$H-NMR (400 MHz, DMSO-d6) δ: 9.54 (s, 1H), 8.35 (s, 1H), 7.79 (s, 1H), 7.66 (dd, 1H, J=10.0, 2.0 Hz), 7.55-7.45 (m, 2H), 7.18 (s, 1H), 4.18 (t, 2H, J=6.4 Hz), 3.94 (s, 3H), 2.56 (t, 2H, J=7.0 Hz), 2.48-2.45 (m, 4H), 1.98-1.90 (m, 2H), 1.78-1.62 (m, 4H).

MS 238, 239 (½M+1).

Example 14

Synthesis of 4-(3-chloro-4-fluoroanilino)-6-methoxy-7-(2-(pyrrolidine-1-yl)ethoxy)quinazoline (Compound 20)

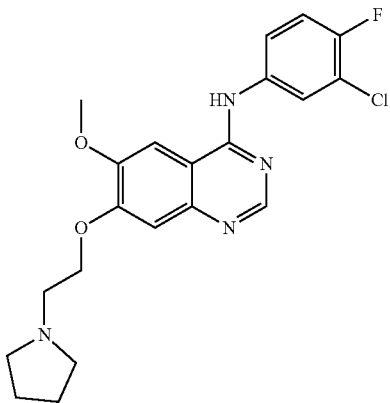 [SMILES: COc1cc2c(Nc3ccc(F)c(Cl)c3)ncnc2cc1OCCN1CCCC1]

4-(3-chloro-4-fluoroanilino)-6-methoxy-7-hydroxyquinazoline trifluoroacetic acid salt (500 mg, 1.15 mmol), N-chloroethylpyrrolidine hydrochloride (294 mg, 1.73 mmol) and potassium carbonate (637 mg, 4.61 mmol) were dispersed in N,N-dimethylformamide (DMF, 5 mL). The mixture was stirred for 18 hours at 80° C. while maintaining the constant temperature. The reaction mixture was cooled to room temperature and poured into water (50 mL). The resulting mixture was extracted with ethyl acetate. The organic layer was dried over anhydrous sodium sulfate, and concentrated under a reduced pressure to obtain a crude product. The crude product was purified by a preparative thin-layer chromatography (methylene chloride:methanol=10:1) to produce a white solid (160 mg, yield: 33%).

$^1$H-NMR (400 MHz, DMSO-d6) δ: 9.61 (s, 1H), 8.50 (s, 1H), 8.14 (dd, 1H, J=7.0, 2.6 Hz), 7.88-7.78 (m, 2H), 7.45 (t, 1H, J=9.0 Hz), 7.24 (s, 1H), 4.33-4.21 (m, 2H), 3.97 (s, 3H), 3.05-2.85 (m, 2H), 2.78-2.55 (m, 4H), 1.73 (m, 4H).

MS 209, 210 (½M+1).

Example 15

Synthesis of 3-(4-(4-bromo-2-fluoroanilino)-6-methoxyquinazolin-7-yl-oxy)propanamide (Compound 22)

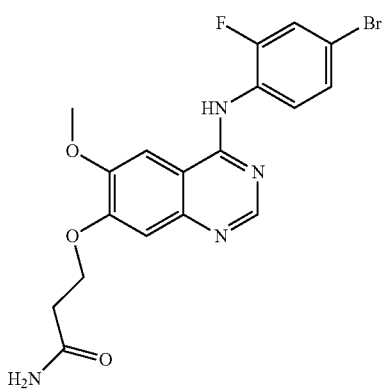 [SMILES: COc1cc2c(Nc3ccc(Br)cc3F)ncnc2cc1OCCC(N)=O]

4-(4-bromo-2-fluoroanilino)-6-methoxy-7-hydroxyquinazoline (1.0 g, 2.75 mmol), acrylamide (1.95 g, 27.5 mmol) and 1,8-diazabicyclo(5.4.0)-undec-7-ene (DBU, 837 mg, 5.50 mmol) were dissolved in ethanol (10 mL) at room temperature. The mixture was stirred for 48 hours to conduct the reaction at 85° C. The resulting reaction mixture was concentrated and purified by a silica gel column chromatography (methylene chloride:methanol=10:1) to produce a yellow solid (151 mg, yield: 13%).

$^1$H-NMR (400 MHz, CD$_3$OD) δ: 8.40 (s, 1H), 7.60-7.40 (m, 4H), 6.63 (s, 1H), 4.58 (t, 2H, J=6.2 Hz), 3.97 (s, 3H), 2.87 (t, 2H, J=6.2 Hz).

MS 435, 437 (M+1).

Example 16

Synthesis of 4-(4-(4-bromo-2-fluoroanilino)-6-methoxyquinazolin-7-yl-oxy)butanamide (Compound 23)

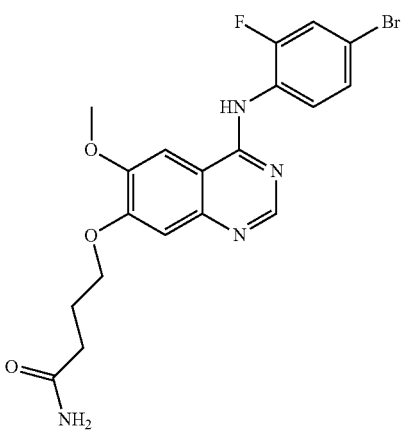 [SMILES: COc1cc2c(Nc3ccc(Br)cc3F)ncnc2cc1OCCCC(N)=O]

4-(4-bromo-2-fluoroanilino)-6-methoxy-7-hydroxyquinazoline trifluoroacetic acid salt (1.5 g, 3.14 mmol), 4-chlorobutanamide (687 mg, 5.65 mmol), tetrabutylammonium iodide (232 mg, 0.63 mmol) and 1,8-diazabicyclo(5.4.0)-undec-7-ene (DBU, 955 mg, 6.28 mmol) were dissolved in N-methyl pyrrolidone (20 mL). The mixture was stirred for 24 hours at 85° C. while maintaining the constant temperature. The reaction mixture was cooled to room temperature and poured into water (150 mL). The resulting mixture was extracted with ethyl acetate. The organic layer was dried over anhydrous sodium sulfate, and concentrated to obtain a crude product. The crude product was purified by a silica gel column chromatography (methylene chloride:methanol=50:1) to produce a light brown solid (110 mg, yield: 8%).

$^1$H-NMR (400 MHz, DMSO-d6) δ: 9.58 (s, 1H), 8.35 (s, 1H), 7.81 (s, 1H), 7.67 (dd, 1H, J=10.0, 1.6 Hz), 7.60-7.40 (m, 2H), 7.37 (br s, 1H), 7.18 (s, 1H), 6.82 (br s, 1H), 4.14 (t, 2H, J=6.4 Hz), 3.95 (s, 3H), 2.27 (t, 2H, J=7.4 Hz), 2.10-1.92 (m, 2H).

MS 449, 451 (M+1).

Example 17

Synthesis of 6-(4-(3-chloro-4-fluoroanilino)-6-methoxyquinazolin-7-yl-oxy)hexanamide (Compound 24)

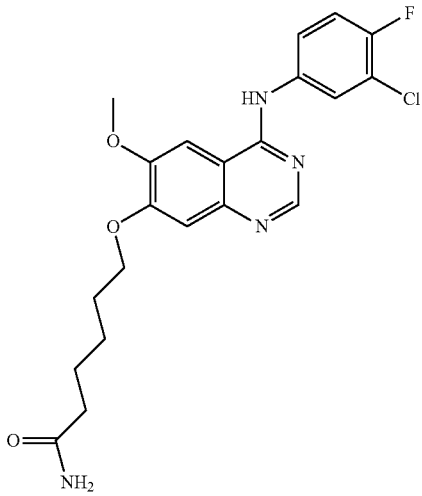 [SMILES: COc1cc2c(Nc3ccc(F)c(Cl)c3)ncnc2cc1OCCCCCC(N)=O]

4-(3-chloro-4-fluoroanilino)-6-methoxy-7-hydroxyquinazoline trifluoroacetic acid salt (500 mg, 1.15 mmol), 6-chlorohexanamide (336 mg, 2.25 mmol) and potassium carbonate (398 mg, 2.88 mmol) were dispersed in N,N-dimethylformamide (DMF, 5 mL) at room temperature. The mixture was stirred for 18 hours at 80° C. while maintaining the constant temperature. The reaction mixture was cooled to room temperature and poured into water (50 mL). The resulting mixture was extracted with ethyl acetate. The organic layer was dried over anhydrous sodium sulfate, and concentrated to obtain a crude product. The crude product was purified by a silica gel column chromatography (methylene chloride:methanol=50:1) to produce a white solid (220 mg, yield: 44%).

$^1$H-NMR (400 MHz, DMSO-d6) δ: 9.55 (s, 1H), 8.50 (s, 1H), 8.13 (dd, 1H, J=6.8, 2.4 Hz), 7.88-7.75 (m, 2H), 7.45 (t, 1H, J=9.0 Hz), 7.25 (br s, 1H), 7.19 (s, 1H), 6.70 (br s, 1H), 4.13 (t, 2H, J=6.6 Hz), 3.97 (s, 3H), 2.08 (t, 2H, J=7.4 Hz), 1.88-1.72 (m, 2H), 1.65-1.50 (m, 2H), 1.50-1.35 (m, 2H).

MS 433, 435 (M+1).

Example 18

Synthesis of 4-(3-chloro-4-fluoroanilino)-6-methoxy-7-(3-(1H-imidazole-1-yl)propoxy)quinazoline (Compound 25)

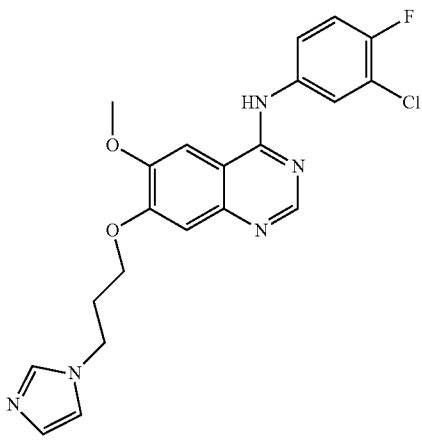 [SMILES: COc1cc2c(Nc3ccc(F)c(Cl)c3)ncnc2cc1OCCCn1ccnc1]

4-(3-chloro-4-fluoroanilino)-6-methoxy-7-hydroxyquinazoline trifluoroacetic acid salt (500 mg, 1.15 mmol), 3-(1H-imidazol-1-yl)-propan-1-ol (400 mg) and triphenylphosphine (454 mg, 1.73 mmol) were dissolved in anhydrous tetrahydrofuran (THF, 10 mL) at room temperature. To the resulting solution was dropwise added diisopropyl azodicarboxylate (DIAD, 350 mg, 1.73 mmol) at room temperature under the protection of nitrogen. After the completion of the dropwise addition, the resulting mixture was stirred for 18 hours at 30° C. to conduct the reaction. The reaction mixture was concentrated to obtain a crude product. The crude product was purified by a silica gel column chromatography (methylene chloride:methanol=50:1) to produce a white solid (107 mg, yield: 22%).

$^1$H-NMR (400 MHz, DMSO-d6) δ: 9.60 (s, 1H), 8.50 (s, 1H), 8.13 (dd, 1H, J=6.8, 2.8 Hz), 7.90-7.75 (m, 2H), 7.64 (s, 1H), 7.45 (t, 1H, J=9.2 Hz), 7.21 (d, 2H, J=11.6 Hz), 6.90 (s, 1H), 4.17 (t, 2H, J=7.0 Hz), 4.10 (t, 2H, J=6.2 Hz), 3.99 (s, 3H), 2.27 (t, 2H, J=6.4 Hz).

MS 428, 430 (M+1).

Example 19

Synthesis of 4-(4-bromo-2-fluoroanilino)-6-methoxy-7-(2-(2-methylthiazol-4-yl)ethoxy)quinazoline (Compound 26)

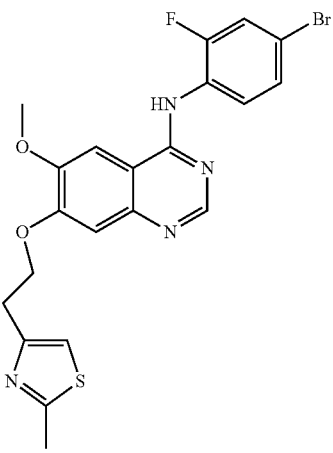 [SMILES: COc1cc2c(Nc3ccc(Br)cc3F)ncnc2cc1OCCc1csc(C)n1]

4-(4-bromo-2-fluoroanilino)-6-methoxy-7-hydroxyquinazoline trifluoroacetic acid salt (800 mg, 1.67 mmol), 2-methyl-4-methylsulfonyloxyethylthiazole (555 mg, 2.51 mmol), and potassium carbonate (578 mg, 4.18 mmol) were dispersed in N,N-dimethylformamide (DMF, 10 mL) at room temperature. The mixture was stirred for 18 hours at 80° C. while maintaining the constant temperature. The reaction mixture was cooled to room temperature and poured into water (50 mL). A solid separated out. The resulting mixture was filtered and dried to obtain a crude product. The crude product was mixed with ethyl acetate to form a slurry. The slurry was filtered and dried to produce a brown solid (320 mg, yield: 39%).

$^1$H-NMR (400 MHz, CDCl$_3$) δ: 8.69 (s, 1H), 8.52 (t, 1H, J=8.6 Hz), 7.40-7.30 (m, 3H), 7.27-7.24 (m, 1H), 7.02-6.92 (m, 2H), 4.51 (t, 2H, J=7.0 Hz), 4.02 (s, 3H), 3.36 (t, 2H, J=6.8 Hz), 2.71 (s, 3H).

MS 489, 491 (M+1).

Example 20

Synthesis of 4-(3-chloro-4-fluoroanilino)-6-methoxy-7-((2-methylthiazol-5-yl)methoxy)quinazoline (Compound 27)

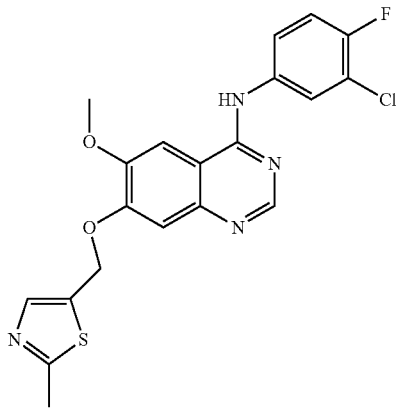 [SMILES: COc1cc2c(Nc3ccc(F)c(Cl)c3)ncnc2cc1OCc1cnc(C)s1]

4-(3-chloro-4-fluoroanilino)-6-methoxy-7-hydroxyquinazoline trifluoroacetic acid salt (500 mg, 1.15 mmol), 2-methyl-5-bromomethylthiazole (332 mg, 1.73 mmol) and potassium carbonate (397 mg, 2.88 mmol) were dispersed in N,N-dimethylformamide (DMF, 5 mL). The mixture was stirred for 18 hours at 60° C. while maintaining the constant temperature. The reaction mixture was cooled to room temperature and poured into water (50 mL). The resulting mixture was extracted with ethyl acetate. The organic layer was dried over anhydrous sodium sulfate and concentrated under a reduced pressure to obtain a crude product. The crude product was purified by a preparative thin-layer chromatography (methylene chloride:methanol=20:1) to produce a white solid (120 mg, yield: 24%).

$^1$H-NMR (400 MHz, CDCl$_3$) δ: 8.60 (s, 1H), 7.92-7.88 (m, 1H), 7.70 (s, 1H), 7.65-7.50 (m, 2H), 7.36 (s, 1H), 7.20-7.10 (m, 2H), 5.37 (s, 2H), 4.04 (s, 3H), 2.71 (s, 3H).

MS 431, 433 (M+1).

Example 21

Synthesis of 4-(3-chloro-4-fluoroanilino)-6-methoxy-7-((2-methylthiazol-4-yl)methoxy)quinazoline (Compound 27')

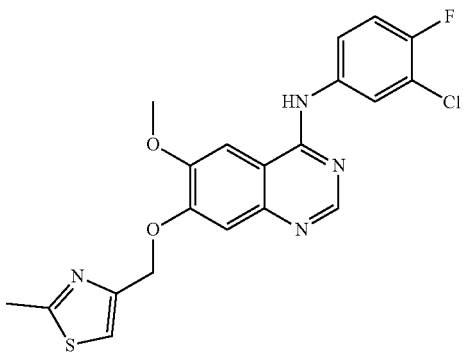 [SMILES: COc1cc2c(Nc3ccc(F)c(Cl)c3)ncnc2cc1OCc1csc(C)n1]

4-(3-chloro-4-fluoroanilino)-6-methoxy-7-hydroxyquinazoline (60 mg, 0.188 mmol), 2-methyl-4-chloromethylthiazole (100 mg, 0.68 mmol) and potassium carbonate (70 mg) were dispersed in N,N-dimethylformamide (DMF, 5 mL). The mixture was heated to 90° C. and stirred for 2 hours to conduct the reaction. After the completion of the reaction, the reaction mixture was cooled to room temperature. Purified water (20 mL) was added. The resulting mixture was extracted with ethyl acetate. The organic layer was dried over anhydrous sodium sulfate, concentrated and purified by a silica gel column chromatography (methylene chloride:methanol=10:1) to obtain the title compound (22 mg).

$^1$H-NMR (600 MHz, DMSO) δ: 9.83 (s, 1H), 8.50 (m, 1H), 8.20 (s, 1H), 7.99-7.88 (m, 2H), 7.64 (s, 1H), 7.45-7.38 (m, 2H), 5.27 (s, 2H), 3.98 (s, 3H), 3.04 (s, 3H).

MS: 431, 433 (M+1).

Example 22

Synthesis of 4-(4-bromo-2-fluoroanilino)-6-methoxy-7-(4-(dimethylamino)-butoxy)quinazoline (Compound 28)

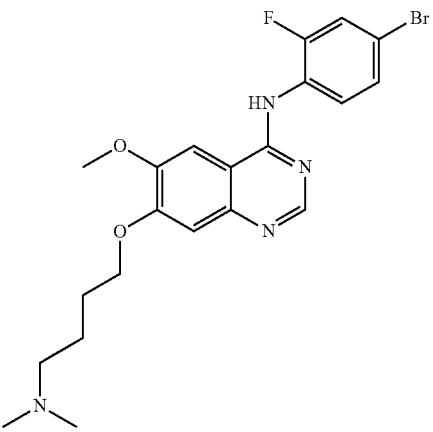

4-(4-bromo-2-fluoroanilino)-6-methoxy-7-hydroxyquinazoline trifluoroacetic acid salt (500 mg, 1.05 mmol), 4-chloro-N,N-dimethylbutan-1-amine hydrochloride (268 mg, 1.57 mmol) and potassium carbonate (362 mg, 2.62 mmol) were added to N,N-dimethylformamide (DMF, 5 mL) at room temperature. The mixture was stirred for 18 hours at 120° C. to conduct the reaction. The reaction mixture was cooled to room temperature and poured into water (50 mL). The resulting mixture was extracted with ethyl acetate and concentrated to obtain a crude product. The crude product was dispersed in an aqueous saturated sodium bicarbonate solution to be neutralized. The resulting mixture was extracted with ethyl acetate. The organic layer was dried over anhydrous sodium sulfate, and concentrated to produce a light brown solid (102 mg, yield: 21%).

$^1$H-NMR (400 MHz, DMSO-d6) δ: 9.59 (s, 1H), 8.35 (s, 1H), 7.82 (s, 1H), 7.66 (d, 1H, J=9.2 Hz), 7.59-7.41 (m, 2H), 7.19 (s, 1H), 4.16 (t, 2H, J=6.6 Hz), 3.95 (s, 3H), 2.39-2.29 (m, 2H), 2.18 (s, 6H), 1.87-1.74 (m, 2H), 1.66-1.53 (m, 2H).

MS 463, 465 (M+1).

Example 23

Synthesis of 4-(4-bromo-2-fluoroanilino)-6-methoxy-7-(3-(dimethylamino)-propoxy)quinazoline (Compound 29)

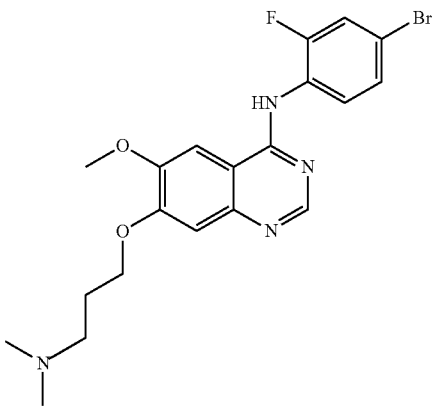

4-(4-bromo-2-fluoroanilino)-6-methoxy-7-hydroxyquinazoline trifluoroacetic acid salt (500 mg, 1.05 mmol), 3-chloro-N,N-dimethylpropan-1-amine hydrochloride (246 mg, 1.57 mmol) and potassium carbonate (362 mg, 2.62 mmol) were added to N,N-dimethylformamide (DMF, 5 mL) at room temperature. The mixture was stirred for 5 hours at 80° C. to conduct the reaction. The reaction mixture was cooled to room temperature and poured into water (80 mL). The resulting mixture was extracted with ethyl acetate. The organic layer was dried over anhydrous sodium sulfate, and concentrated to obtain a crude product. The crude product was purified by a silica gel column chromatography (methylene chloride:methanol=10:1) to produce a white solid (180 mg, yield: 38%).

$^1$H-NMR (400 MHz, DMSO-d6) δ: 9.75 (s, 1H), 8.35 (s, 1H), 7.90 (s, 1H), 7.65 (d, 1H, J=9.6 Hz), 7.59-7.41 (m, 2H), 7.18 (s, 1H), 4.18 (t, 2H, J=6.2 Hz), 3.96 (s, 3H), 2.61-2.51 (m, 2H), 2.29 (s, 6H), 2.07-1.94 (m, 2H).

MS 225, 226 (½M+1).

Example 24

Synthesis of 4-(4-bromo-2-fluoroanilino)-6-methoxy-7-(4-(pyrrolidin-1-yl)butoxy)quinazoline (Compound 30)

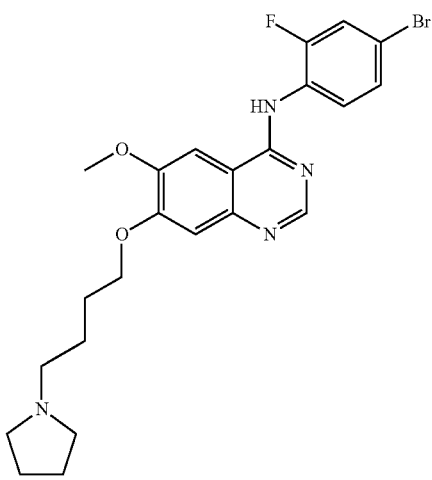

4-(4-bromo-2-fluoroanilino)-6-methoxy-7-hydroxyquinazoline trifluoroacetic acid salt (500 mg, 1.05 mmol), N-hydroxybutylpyrrolidine (600 mg) and triphenylphosphine (413 mg, 1.58 mmol) were dissolved in tetrahydrofuran (THF, 10 mL) at room temperature. The resulting mixture was cooled to 0-5° C. To the mixture was dropwise added diisopropyl azodicarboxylate (DIAD, 319 mg, 1.58 mmol). The resulting mixture was stirred for 18 hours at 40° C. to conduct the reaction. The reaction mixture was concentrated and purified by a silica gel column chromatography (methylene chloride:methanol=10:1) to obtain a crude product. The crude product was dispersed in an aqueous saturated sodium bicarbonate solution to be neutralized and then the mixture was extracted with ethyl acetate. The organic layer was dried over anhydrous sodium sulfate, and concentrated to produce a light brown solid (120 mg, yield: 23%).

$^1$H-NMR (400 MHz, DMSO-d6) δ: 9.54 (s, 1H), 8.35 (s, 1H), 7.80 (s, 1H), 7.66 (dd, 1H, J=10.0, 2.0 Hz), 7.57-7.43 (m, 2H), 7.19 (s, 1H), 4.16 (t, 2H, J=6.4 Hz), 3.94 (s, 3H), 2.49-2.35 (m, 6H), 1.89-1.76 (m, 2H), 1.73-1.57 (m, 6H).

MS 245, 246 (½M+1).

Example 25

Synthesis of N-methyl-6-(4-(4-bromo-2-fluoroanilino)-6-methoxyquinazolin-7-yloxy)hexanamide (Compound 31)

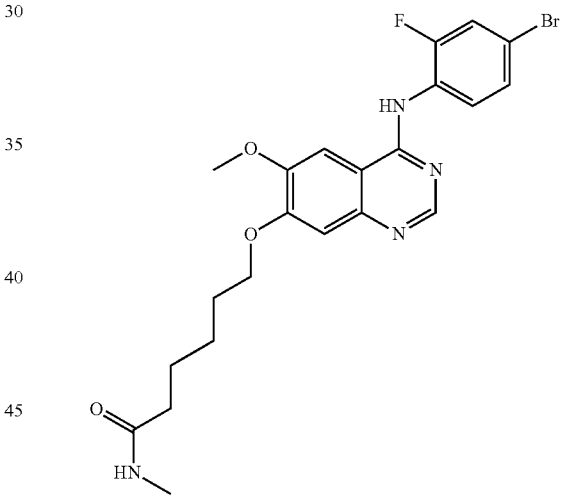

4-(4-bromo-2-fluoroanilino)-6-methoxy-7-hydroxyquinazoline (728 mg, 2 mmol), N-methyl-6-bromohexanamide (416 mg, 2 mmol) and potassium carbonate (690 mg, 5 mmol) were dispersed in N,N-dimethylformamide (DMF, 10 mL). The resulting mixture was heated to reflux and stirred for 18 hours to conduct the reaction. The reaction mixture was cooled to room temperature and poured into water (100 mL). The resulting mixture was extracted with ethyl acetate. The organic layer was dried over anhydrous sodium sulfate, and concentrated to obtain a crude product (500 mg). The crude product was re-crystallized with methanol and filtered to produce a white solid (230 mg, yield: 23%).

$^1$H-NMR (400 MHz, DMSO-d6) δ: 9.55 (s, 1H), 8.35 (s, 1H), 7.83-7.63 (m, 3H), 7.57-7.44 (m, 2H), 7.18 (s, 1H), 4.12 (t, 1H, J=6.4 Hz), 3.94 (s, 3H, J=11.6 Hz), 2.56 (d, 3H, J=4.8 Hz), 2.09 (t, 3H, J=6.4 Hz), 1.79 (m, 2H), 1.58 (m, 2H), 1.42 (m, 2H).

MS 491, 493 (M+1).

Example 26

Synthesis of N,N-dimethyl-6-(4-(4-bromo-2-fluoroanilino)-6-methoxy-quinazolin-7-yloxy)hexanamide (Compound 32)

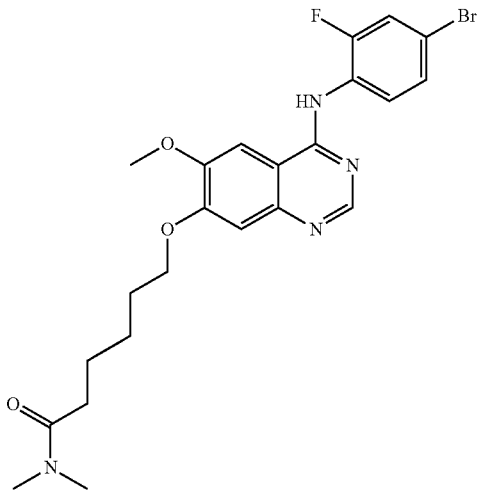

4-(4-bromo-2-fluoroanilino)-6-methoxy-7-hydroxyquinazoline (364 mg, 1.0 mmol), N, N-dimethyl-6-bromohexanamide (222 mg, 1.0 mmol) and potassium carbonate (276 mg, 2.0 mmol) were dispersed in N,N-dimethylformamide (DMF, 10 mL) at room temperature. The mixture was heated to 80° C. and stirred for 3 hours while maintaining the constant temperature. To the reaction mixture was added water (50 mL). The resulting mixture was extracted with ethyl acetate. The organic layer was dried over anhydrous sodium sulfate, and concentrated under a reduced pressure to obtain a crude product. The crude product was re-crystallized with methanol to produce a white solid (160 mg, yield: 32%).

$^1$H-NMR (400 MHz, DMSO-d6) δ: 9.54 (br s, 1H), 8.35 (s, 1H), 7.79 (s, 1H), 7.67 (dd, 1H, J=10.0, 2.0 Hz), 7.7.58-7.41 (m, 2H), 4.13 (t, 2H, J=6.4 Hz), 3.94 (s, 3H), 2.96 (s, 3H), 2.81 (s, 3H), 2.32 (t, 2H, J=7.2 Hz), 1.88-1.75 (m, 2H), 1.64-1.40 (m, 4H).

MS 505, 507 (M+1).

Example 27

Synthesis of 5-(4-(4-bromo-2-fluoroanilino)-6-methoxyquinazolin-7-yl-oxy)pentanamide (Compound 33)

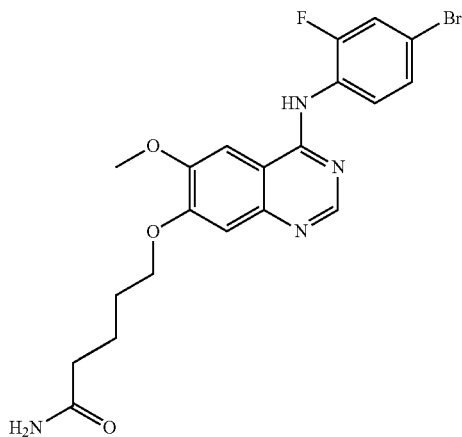

4-(4-bromo-2-fluoroanilino)-6-methoxy-7-hydroxyquinazoline (1.8 g, 4.95 mmol), 5-bromopentanamide (1.78 g, 9.89 mmol) and potassium carbonate (1.8 g, 13.02 mmol) were added into N,N-dimethylformamide (DMF, 15 mL) at room temperature. The mixture was heated to 50° C. and stirred for 2 hours to conduct the reaction. To the reaction mixture was added water (30 mL). The resulting mixture was extracted with ethyl acetate. The organic layer was dried over anhydrous sodium sulfate, and concentrated to obtain a crude product. The crude product was re-crystallized with methanol to produce the title compound (1.4 g, yield: 61%).

$^1$H-NMR (600 MHz, DMSO-d6) δ: 9.53 (s, 1H), 8.35 (s, 1H), 7.79 (s, 1H), 7.66 (dd, 1H, J=10.2 2.4 Hz), 7.54 (t, 1H, J=2.4 Hz), 7.46 (dd, 1H, J=8.4, 1.2 Hz) 7.28 (br s, 1H), 7.19 (s, 1H), 6.74 (br s, 1H), 4.14 (t, 2H, J=6.6 Hz), 3.95 (s, 3H), 2.15 (t, 2H, J=7.2 Hz), 1.81-1.78 (m, 2H), 1.69-1.67 (m, 2H).

MS: m/z 463.4, 465.3 (M+1)

Example 28

Synthesis of 4-(4-bromo-2-fluoroanilino)-6-methoxy-7-(2-(1H-imidazol-1-yl)ethoxy)quinazoline (Compound 34)

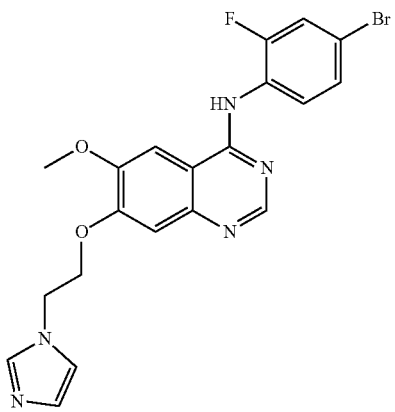 [SMILES: COc1cc2c(Nc3ccc(Br)cc3F)ncnc2cc1OCCn1ccnc1]

4-(4-bromo-2-fluoroanilino)-6-methoxy-7-hydroxyquinazoline (1.00 g, 2.75 mmol), 1-(2-chloroethyl)-1H-imidazole (0.72 g, 5.5 mmol) and potassium carbonate (0.95 g, 6.88 mmol) were added to N,N-dimethylformamide (DMF, 15 mL) at room temperature. The mixture was heated to 60° C. and stirred for 3 hours to conduct the reaction. After the completion of the reaction, to the reaction mixture was added water (30 mL). The resulting mixture was extracted with ethyl acetate. The organic layer was dried over anhydrous sodium sulfate, and concentrated to obtain a crude product. The crude product was re-crystallized with methanol to produce the title compound (0.91 g, yield: 72%).

$^1$H-NMR (600 MHz, DMSO-d6) δ: 9.56 (s, 1H), 8.36 (s, 1H), 7.82 (s, 1H), 7.72-7.65 (m, 2H), 7.53-7.46 (m, 2H), 7.29-7.23 (m, 2H), 6.91 (s, 1H), 4.45 (m, 4H), 3.95 (s, 3H).

MS: m/z 458.4, 460.4 (M+1)

Example 29

Synthesis of 4-(3-chloro-4-fluoroanilino)-6-methoxy-7-(2-(1H-imidazol-1-yl)ethoxy)quinazoline (Compound 36)

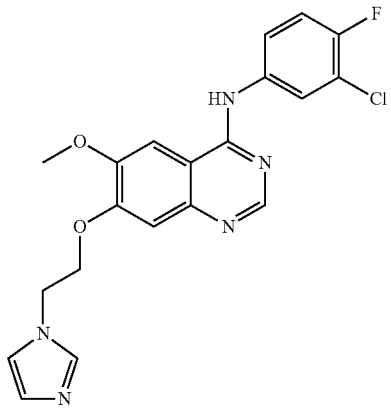 [SMILES: COc1cc2c(Nc3ccc(F)c(Cl)c3)ncnc2cc1OCCn1ccnc1]

4-(3-chloro-4-fluoroanilino)-6-methoxy-7-hydroxyquinazoline trifluoroacetic acid salt (500 mg, 1.15 mmol), 1-(2-chloroethyl)-1H-imidazole hydrochloride (289 mg, 1.73 mmol) and potassium carbonate (636 g, 4.60 mmol) were dispersed in N,N-dimethylformamide (DMF, 5 mL) at room temperature. The mixture was heated to 80° C. and stirred for 18 hours to conduct the reaction. The reaction mixture was cooled to room temperature and poured into water (100 mL). The resulting mixture was extracted with ethyl acetate. The organic layer was dried over anhydrous sodium sulfate, and concentrated to obtain a crude product. The crude product was purified by a silica gel column chromatography (methylene chloride:methanol=10:1) to produce a light yellow solid (120 mg, yield: 25%).

$^1$H-NMR (400 MHz, DMSO-d6) δ: 9.58 (br s, 1H), 8.50 (s, 1H), 8.13 (dd, 1H, J=7.0, 2.6 Hz), 7.85-7.76 (m, 2H), 7.72 (s, 1H), 7.45 (t, 1H, J=9.2 Hz), 7.29 (s, 1H), 7.24 (s, 1H), 6.90 (s, 1H), 4.45 (s, 4H), 3.97 (s, 3H).

MS 207.5, 208.5 (½M+1).

Example 30

Synthesis of 4-(3-chloro-4-fluoroanilino)-6-methoxy-7-(4-(dimethylamino)-butoxy)quinazoline (Compound 37)

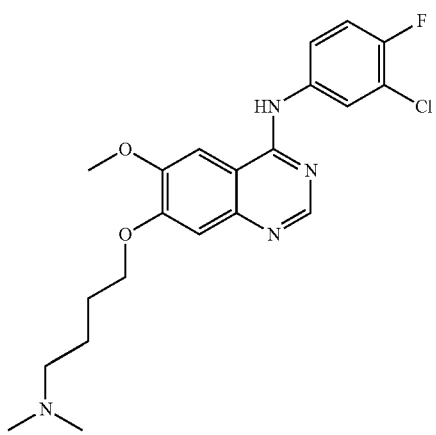

Step 1: Synthesis of 4-(3-chloro-4-fluoroanilino)-6-methoxy-7-((4-acetyl-oxy)butoxy)quinazoline 4-(3-chloro-4-fluoroanilino)-6-methoxy-7-hydroxyquinazoline (10 g, 31.3 mmol) was dissolved in N,N-dimethylformamide (DMF, 100 mL) at room temperature. To the resulting mixture were added potassium carbonate (13 g, 93.9 mmol) and 4-bromobutyl acetate (7.3 g, 37.6 mmol). The mixture was reacted for 2 hours at 50° C. The reaction mixture was cooled to room temperature and poured into water (200 mL). The resulting mixture was extracted with dichloromethane. The organic layer was dried over anhydrous sodium sulfate, and concentrated to produce a yellow oil (12 g), which was directly used in the next step.

Step 2: Synthesis of 4-(3-chloro-4-fluoroanilino)-6-methoxy-7-(4-hydroxy-butoxy)quinazoline The product of Step 1 (12 g) was dissolved in methanol (50 mL). To the mixture were added water (10 mL) and lithium hydroxide monohydrate (1.4 g, 33.2 mmol). The resulting mixture was reacted at room temperature overnight. The reaction mixture was concentrated. To the resulting mixture were added water (200 mL) and ethyl acetate (40 mL). While the mixture was stirred, a solid separated out. The mixture was filtered and the resulting filter cake was dried to produce a yellow solid (6.2 g, yield: 51%).

Step 3: Synthesis of 4-(3-chloro-4-fluoroanilino)-6-methoxy-7-((4-methyl-sulfonyloxy)butoxy)quinazoline The product of Step 2 (6.2 g, 15.8 mmol) was dissolved in dichloromethane (50 mL). To the mixture was added triethylamine (3.2 g, 31.6 mmol), and then dropwise added methylsulfonyl chloride (2.7 g, 23.7 mmol) in an ice-bath. After the completion of the dropwise addition, the resulting mixture was reacted for 3 hours at room temperature. To the reaction mixture was added water (150 mL). The mixture was extracted with dichloromethane. The organic layer was dried over anhydrous sodium sulfate, and concentrated to produce a yellow solid (7.2 g, yield: 96%).

Step 4: Synthesis of 4-(3-chloro-4-fluoroanilino)-6-methoxy-7-(4-(di-methylamino)butoxy)quinazoline The product of Step 3 (2.5 g, 5.3 mmol), dimethylamine hydrochloride (644 mg, 7.95 mmol) and potassium carbonate (2.9 g, 21.2 mmol) were dispersed in acetonitrile (15 mL) at room temperature. The mixture was stirred at 80° C. overnight. The reaction mixture was concentrated. To the resulting mixture was added water (100 mL). The mixture was extracted with dichloromethane. The organic layer was dried over anhydrous sodium sulfate, and concentrated to obtain a crude product. The crude product was purified by a silica gel column chromatography (methylene chloride:methanol=10:1) to produce a light yellow solid (700 mg, yield: 32%).

$^1$H-NMR (400 MHz, DMSO-d6) δ: 9.56 (br s, 1H), 8.50 (s, 1H), 8.13 (dd, 1H, J=6.8, 2.8 Hz), 7.85-7.77 (m, 2H), 7.45 (t, 1H, J=9.2 Hz), 7.20 (s, 1H), 4.16 (t, 2H, J=56.4 Hz), 3.97 (s, 3H), 2.27 (t, 2H, J=7.2 Hz), 2.13 (s, 6H), 1.83-1.78 (m, 2H), 1.60-1.60 (m, 2H).

MS 210, 211 (½M+1).

Example 31

Synthesis of 4-(3-chloro-4-fluoroanilino)-6-methoxy-7-(3-(dimethylamino)-propoxy)quinazoline (Compound 38)

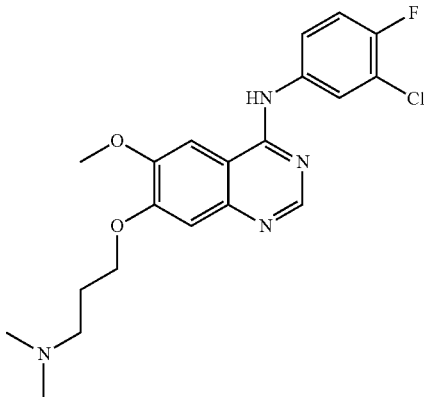 [SMILES: COc1cc2c(Nc3ccc(F)c(Cl)c3)ncnc2cc1OCCCN(C)C]

4-(3-chloro-4-fluoroanilino)-6-methoxy-7-hydroxyquinazoline (2 g, 6.26 mmol), 3-chloro-N, N-dimethylpropan-1-amine hydrochloride (1.2 g, 7.51 mmol) and potassium carbonate (3.5 g, 25.04 mmol) were dispersed in N,N-dimethylformamide (DMF, 20 mL). The mixture was stirred at 80° C. overnight. The reaction mixture was cooled to room temperature and poured into water (80 mL). The resulting mixture was extracted with dichloromethane. The organic layer was dried over anhydrous sodium sulfate, and concentrated to obtain a crude product. The crude product was purified by a silica gel column chromatography (methylene chloride:methanol=10:1) to produce a yellow solid (325 mg, yield: 13%).

$^1$H-NMR (400 MHz, DMSO-d6) δ: 10.08 (br s, 1H), 8.49 (s, 1H), 8.29 (dd, 1H, J=6.8, 2.4 Hz), 8.14 (s, 1H), 8.01-7.97 (m, 1H), 7.42 (t, 1H, J=9.2 Hz), 7.17 (s, 1H), 4.17 (t, 2H, J=6.4 Hz), 4.01 (s, 3H), 2.42 (t, 2H, J=7.0 Hz), 2.19 (s, 6H), 1.98-1.91 (m, 2H).

MS 203, 204 (½M+1).

Example 32

Synthesis of 4-(3-chloro-4-fluoroanilino)-6-methoxy-7-(3-(pyrrolidin-1-yl)propoxy)quinazoline (Compound 39)

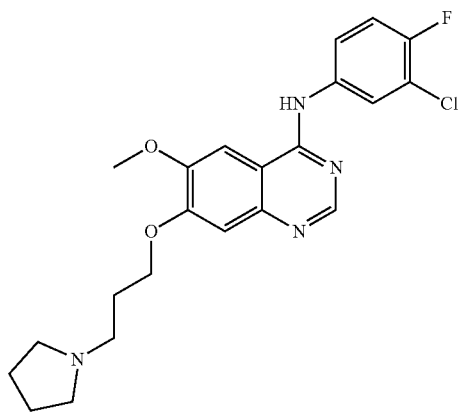 [SMILES: COc1cc2c(Nc3ccc(F)c(Cl)c3)ncnc2cc1OCCCN1CCCC1]

4-(3-chloro-4-fluoroanilino)-6-methoxy-7-hydroxyquinazoline (2 g, 6.26 mmol), N-chloropropylpyrrolidine hydrochloride (1.72 g, 9.39 mmol) and potassium carbonate (2.59 g, 18.78 mmol) were dispersed in N,N-dimethylformamide (DMF, 10 mL). The mixture was stirred at 80° C. overnight. The reaction mixture was cooled to room temperature and poured into water (50 mL). The resulting mixture was extracted with dichloromethane. The organic layer was dried over anhydrous sodium sulfate, and concentrated to obtain a crude product. The crude product was purified by a silica gel column chromatography (methylene chloride:methanol=10:1) to produce a yellow solid (400 mg, yield: 15%).

$^1$H-NMR (400 MHz, DMSO-d6) δ: 9.59 (s, 1H), 8.51 (s, 1H), 8.14 (dd, 1H, J=7.0, 2.4 Hz), 7.87-7.76 (m, 2H), 7.45 (t, 1H, J=9.0 Hz), 7.20 (s, 1H), 4.20 (t, 2H, J=6.2 Hz), 3.98 (s, 3H), 2.62-2.53 (m, 4H), 2.02-1.99 (m, 2H), 1.73 (m, 4H).

MS 216, 217 (½M+1).

Example 33

Synthesis of 4-(3-chloro-4-fluoroanilino)-6-methoxy-7-(4-(pyrrolidin-1-yl)butoxy)quinazoline (Compound 40)

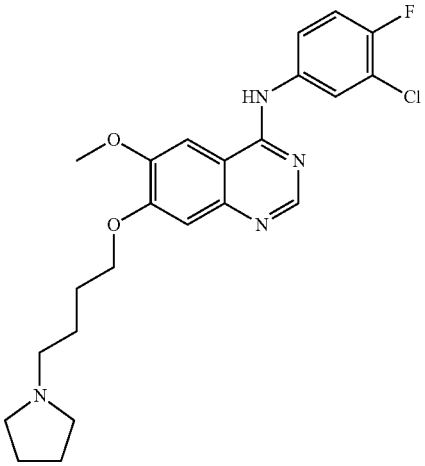 [SMILES: COc1cc2c(Nc3ccc(F)c(Cl)c3)ncnc2cc1OCCCCN1CCCC1]

Steps 1, 2, and 3 were identical to those for preparing Compound 37.

Step 4

Synthesis of 4-(3-chloro-4-fluoroanilino)-6-methoxy-7-(4-(pyrrolidin-1-yl)butoxy)quinazoline The product of Step 3 (3.0 g, 6.4 mmol), tetrahydropyrrole (681.6 mg, 9.6 mmol) and potassium carbonate (2.6 g, 19.2 mmol) were dispersed in acetonitrile (20 mL) at room temperature. The mixture was stirred at 80° C. overnight. The reaction mixture was concentrated. To the resulting mixture was added water (100 mL). The mixture was extracted with dichloromethane. The organic layer was dried over anhydrous sodium sulfate, and concentrated to obtain a crude product. The crude product was purified by a silica gel column chromatography (methylene chloride:methanol=10:1) to produce a light yellow solid (500 mg, yield: 18%).

$^1$H-NMR (400 MHz, DMSO-d6) δ: 9.62 (br s, 1H), 8.49 (s, 1H), 8.13 (dd, 1H, J=6.8, 2.4 Hz), 7.85-7.77 (m, 2H), 7.44 (t, 1H, J=9.0 Hz), 7.19 (s, 1H), 4.16 (t, 2H, J=6.6 Hz), 3.96 (s, 3H), 2.50-2.40 (m, 6H), 1.85-1.81 (m, 2H), 1.68-1.60 (m, 6H).

MS 223, 224 (½M+1).

Example 34

Synthesis of 5-(4-(3-chloro-4-fluoroanilino)-6-methoxyquinazolin-7-yl-oxy)pentanamide (Compound 41)

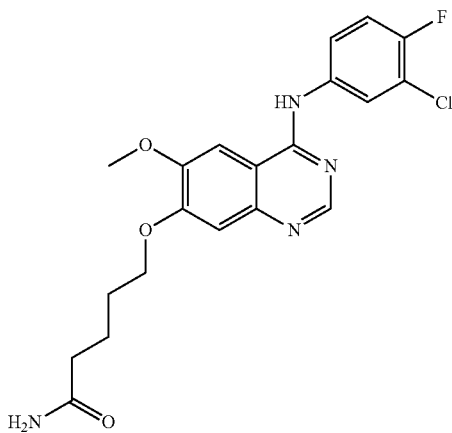 [SMILES: COc1cc2c(Nc3ccc(F)c(Cl)c3)ncnc2cc1OCCCCC(N)=O]

To a 25 mL single-neck flask were successively added 5-bromopentanamide (193 mg, 1.07 mmol), 4-(3-chloro-4-fluoroanilino)-6-methoxy-7-hydroxyquinazoline trifluoroacetic acid salt (420 mg, 0.97 mmol), potassium carbonate (401 mg, 2.91 mmol), potassium iodide (32 mg, 0.19 mmol) and N,N-dimethylformamide (DMF, 5 mL) at room temperature. The mixture was warmed up to 80° C. and reacted overnight. The reaction mixture was poured into ice-water (20 mL). The resulting mixture was filtered. The filter cake was dried to produce a yellow solid (120 mg, yield: 30%).

$^1$H-NMR (400 MHz, DMSO-d6) δ: 9.56 (br s, 1H), 8.50 (s, 1H), 8.12 (dd, 1H, J=6.8, 2.4 Hz), 7.84-7.77 (m, 2H), 7.45 (t, 1H, J=9.0 Hz), 7.28 (br s, 1H), 7.20 (s, 1H), 6.74 (br s, 1H), 4.15 (t, 2H, J=6.2 Hz), 3.97 (s, 3H), 2.14 (t, 2H, J=7.4 Hz), 1.86-1.62 (m, 4H).

MS: 419 (M+1).

Example 35

Synthesis of N-methyl-6-(4-(3-chloro-4-fluoroanilino)-6-methoxy-quinazolin-7-yloxy)hexanamide (Compound 42)

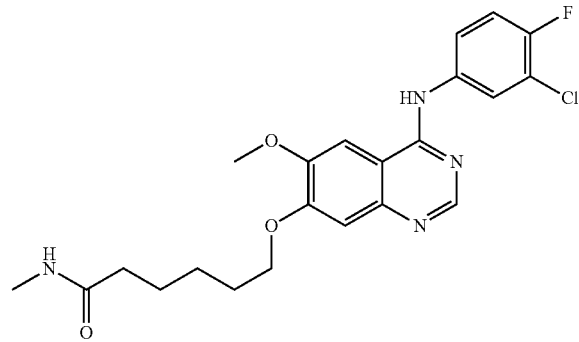 [SMILES: CNC(=O)CCCCCOc1cc2ncnc(Nc3ccc(F)c(Cl)c3)c2cc1OC]

4-(3-chloro-4-fluoroanilino)-6-methoxy-7-hydroxyquinazoline trifluoroacetic acid salt (867 mg, 2 mmol), N-methyl-6-bromohexanamide (416 mg, 2 mmol) and potassium carbonate (690 mg, 5 mmol) were dispersed in N,N-dimethylformamide (DMF, 10 mL). The resulting mixture was heated to reflux and stirred for 18 hours to conduct the reaction. The reaction mixture was cooled to room temperature and poured into water (100 mL). The resulting mixture was extracted with ethyl acetate. The organic layer was dried over anhydrous sodium sulfate, and concentrated to obtain a crude product (500 mg). The crude product was re-crystallized with methanol and filtered to produce a white solid (130 mg, yield: 15%).

$^1$H-NMR (400 MHz, DMSO-d6) δ: 9.57 (s, 1H), 8.50 (s, 1H), 8.13 (dd, 1H, J=6.8, 2.4 Hz), 7.83-7.72 (m, 3H), 7.45 (t, 1H, J=9.0 Hz), 7.19 (s, 1H), 4.13 (t, 2H, J=6.4 Hz), 3.97 (s, 3H, J=4.8 Hz), 2.56 (d, 3H, J=4.4 Hz), 2.09 (t, 2H, J=7.4 Hz), 1.79 (m, 2H), 1.58 (m, 2H), 1.42 (m, 2H).

MS 447 (M+1).

Example 36

Synthesis of N,N-dimethyl-6-(4-(3-chloro-4-fluoroanilino)-6-methoxy-quinazolin-7-yloxy)hexanamide (Compound 43)

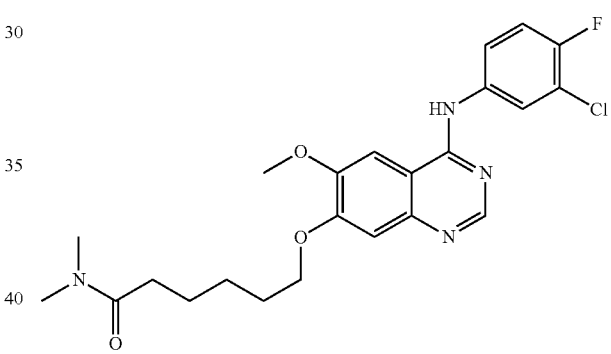

4-(3-chloro-4-fluoroanilino)-6-methoxy-7-hydroxyquinazoline (320 mg, 1.0 mmol), N,N-dimethyl-6-bromohexanamide (222 mg, 1.0 mmol) and potassium carbonate (276 mg, 2 mmol) were dispersed in N,N-dimethylformamide (DMF, 10 mL). The mixture was warmed up to 80° C. and stirred for 3 hours to conduct the reaction. To the reaction mixture was added water (100 mL). The resulting mixture was extracted with ethyl acetate. The organic layer was dried over anhydrous sodium sulfate, and concentrated to obtain a crude product. The crude product was re-crystallized with methanol and filtered to produce a white solid (120 mg, yield: 26%).

$^1$H-NMR (400 MHz, DMSO-d6) δ: 9.56 (s, 1H), 8.50 (s, 1H), 8.14-8.12 (dd, 1H, J=6.8, 2.8 Hz), 7.84-7.78 (m, 2H), 7.45 (t, 1H, J=9.2 Hz), 7.20 (s, 1H), 4.14 (t, 2H, J=6.4 Hz), 3.97 (s, 3H), 2.96 (s, 3H), 2.81 (s, 3H), 2.32 (t, 2H, J=7.2 Hz), 1.88-1.75 (m, 2H), 1.64-1.40 (m, 4H).

MS 461 (M+1).

Reference Example 1

Synthesis of 4-(2-fluoro-4-chloroanilino)-6-methoxy-7-(3-(pyrrolidin-1-yl)-propoxy)quinazoline (Compound 44)

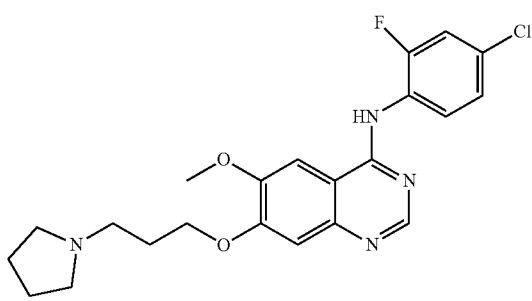 [SMILES: COc1cc2c(Nc3ccc(Cl)cc3F)ncnc2cc1OCCCN1CCCC1]

Step 1: Synthesis of 4-(2-fluoro-4-chloroanilino)-6-methoxy-7-benzyloxy-quinazoline 6-methoxy-7-benzyloxyquinazoline-4-one (6.5 g, 23.0 mmol) was added to toluene (60 mL). To the resulting mixture was added tributylamine (5.2 g, 27.6 mmol). The mixture was heated to 60° C. To the heated mixture was dropwise added phosphorus oxychloride (3.5 g, 23.0 mmol). After the completion of the dropwise addition, the resulting mixture was warmed up to 120° C. and stirred for 1 hour to conduct the reaction. The reaction mixture was cooled down to 57° C. To the cooled mixture was added 4-chloro-2-fluoroaniline (5.0 g, 34.4 mmol). The resulting mixture was then heated to 95° C. and reacted for 0.5 hour. The reaction mixture was cooled to room temperature and filtered to obtain a light yellow product (8.0 g, yield 84.8%).

Step 2: Synthesis of 4-(2-fluoro-4-chloroanilino)-6-methoxy-7-hydroxy-quinazoline To a three-neck flask was added 4-(2-fluoro-4-chloroanilino)-6-methoxy-7-benzyloxyquinazoline (6.0 g, 14.6 mmol), and then trifluoroacetic acid (30 mL) was added. The mixture was stirred until dissolved, heated to 75° C. and reacted for 1 hour. After the completion of the reaction, the reaction mixture was cooled to room temperature, and then concentrated under a reduced pressure to obtain an oily substance. Upon adding methyl tert-butyl ether (150 mL) to the oily substance, a solid separated out. The mixture was filtered and dried to produce a light yellow solid (4.0 g, yield: 85.8%).

Step 3: Synthesis of 4-(2-fluoro-4-chloroanilino)-6-methoxy-7-(3 (pyrrolidin-1-yl)propoxy)quinazoline At room temperature, to a three-neck flask were added 4-(2-fluoro-4-chloroanilino)-6-methoxy-7-hydroxyquinazoline (1.4 g, 4.4 mmol), N-chloro-propylpyrrolidine hydrochloride (809 mg, 4.04 mmol), and potassium carbonate (1.2 g, 8.8 mmol), and then added N,N-dimethylformamide (DMF, 20 mL). The mixture was heated to 80° C., and stirred for 18 hours to conduct the reaction. After the completion of the reaction, the reaction mixture was cooled down to room temperature. To the reaction mixture was added purified water (50 mL). The resulting mixture was extracted with ethyl acetate. The organic layer was dried over anhydrous sodium sulfate, and concentrated to obtain a crude product. The crude product was purified by a preparative thin-layer chromatography (methylene chloride:methanol=10:1) to produce a white solid (1.0 g, yield: 53%).

$^1$H-NMR (600 MHz, DMSO-d6) δ:9.55 (s, 1H), 8.36 (s, 1H), 7.80 (s, 1H), 7.55-7.61 (m, 2H), 7.35-7.36 (m, 1H), 7.19 (s, 1H), 4.18-4.20 (m, 2H), 3.95 (s, 3H), 2.56-2.58 (m, 2H), 2.46-2.51 (m, 4H), 1.95-1.99 (m, 2H), 1.69 (s, 4H).

MS 431.2 (M+1).

Reference Example 2

Synthesis of 4-(2-fluoro-4-bromoanilino)-6-methoxy-7-(3-(piperidin-1-yl)-propoxy)quinazoline (Compound 45)

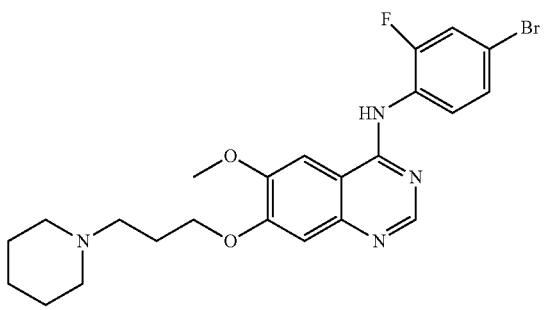 [SMILES: COc1cc2c(Nc3ccc(Br)cc3F)ncnc2cc1OCCCN1CCCCC1]

Step 1: Synthesis of methyl 3-(piperidin-1-yl)propanoate

To a three-neck flask was added piperidine (5 g, 58.7 mmol), and then added methyl acrylate (15 mL). The mixture was warmed up to 80° C. and reacted for 2 hours. After the completion of the reaction, the reaction mixture was cooled down to room temperature, and concentrated under a reduced pressure to produce a yellow oil (10 g), which was directly used in the next step.

Step 2: Synthesis of 3-(piperidin-1-yl)propanol

To a three-neck flask was added anhydrous tetrahydrofuran (80 mL), and then the environment was cooled to 0° C. To the flask was added in batch lithium aluminum hydride (3.5 g, 93.4 mmol), and then dropwise added a solution of methyl 3-(piperidin-1-yl)propanoate (8.0 g, 46.7 mmol) in tetrahydrofuran. After the completion of the dropwise addition, the mixture was warmed up to room temperature and reacted for 2 hours. After the completion of the reaction, the reaction mixture was cooled down to 0° C. To the cooled mixture were successively added purified water (10 mL), an aqueous NaOH solution (15%, 10 mL) and purified water (30 mL). A white solid separated out. The resulting mixture was filtered. The filtrate was concentrated to produce a yellow oil (4.0 g), which was directly used in the next step.

Step 3: Synthesis of 3-(piperidin-1-yl)propyl 4-methyl-benzenesulfonate 3-(Piperidin-1-yl)propanol (3.0 g, 20.9 mmol) was added to dichloro-methane (30 mL). The resulting mixture was cooled down to 0° C. To the cooled mixture were successively added an aqueous triethylamine solution (4.2 g, 41.8 mmol) and tosyl chloride (4.0 g, 20.9 mmol). The mixture was reacted for 4 hours at 0° C. After the completion of the reaction, the reaction mixture was heated to room temperature. To the reaction mixture was added purified water (50 mL). The resulting mixture was separated into two layers, and the aqueous layer was extracted with dichloromethane. The organic layer was dried over anhydrous sodium sulfate, and concentrated to produce a yellow oil (3.0 g), which was directly used in the next step without a further treatment.

Step 4: Synthesis of 4-(2-fluoro-4-bromoanilino)-6-methoxy-7-(3-(piperidin-1-yl)propoxy)quinazoline 4-(2-fluoro-4-bromoanilino)-6-methoxy-7-hydroxyquinazoline (2.0 g, 5.6 mmol), 3-(piperidin-1-yl)propyl4-methylbenzenesulfonate (2.0 g, 6.7 mmol) and potassium carbonate (1.2 g, 8.4 mmol) were added to DMF (15 mL). The mixture was heated to 80° C. and stirred for 2 hours to conduct the reaction. After the completion of the reaction, purified water (50 mL) was added to the reaction mixture. The resulting mixture was extracted with ethyl acetate. The organic layer was dried over anhydrous sodium sulfate, and concentrated to obtain a crude product. The crude product was purified by a preparative thin-layer chromatography (methylene chloride:methanol=10:1) to produce a white solid (1.0 g, yield: 36.5%).

$^1$H-NMR (600 MHz, DMSO-d6) δ:9.57 (s, 1H), 8.35 (s, 1H), 7.81 (s, 1H), 7.56-7.58 (m, 2H), 7.34-7.35 (m, 1H), 7.11 (s, 1H), 4.15-4.19 (m, 2H), 3.94 (s, 3H), 2.42-2.49 (m, 4H), 2.00 (s, 2H), 1.42-1.66 (m, 8H).

MS 490.3 (M+1).

BIOLOGICAL EXAMPLES

Assay 1: In Vitro Cell Experiment

Cell Lines:

TABLE 1

Cell lines and growth medium

| Cell line | Source | Type | Growth medium |
|---|---|---|---|
| A431 | Shanghai Institutes for Biological Sciences of the Chinese Academy of Sciences | Human epidermoid carcinoma (EGFR$_1$ overexpressing) | DMEM with 10% FBS |
| HCC827 | Chinese Academy of Medical Sciences | Human non-small cell lung carcinoma (EGFR$_1$ 19 exon mutation) | RPMI-1640 with 10% FBS |
| A549 | Shanghai Genechem Co., Ltd. | Human non-small-cell lung carcinoma cells (EGFR$_1$ wildtype) | F12K with 10% FBS |
| A375 | Chinese Academy of Medical Sciences | Human melanoma cells (KDR expressing) | RPMI-1640 with 10% FBS |
| HT-29 | Shanghai Institutes for Biological Sciences of the Chinese Academy of Sciences | Human colon carcinoma cells (expressing both c-KIT and PDGFR) | Mycoy's 5A with 10% FBS |
| H292 | Sichuan University | Human lung carcinoma cells (EGFR$_1$ overexpressing) | RPMI-1640 with 10% FBS |
| PC-9 | Sichuan University | Human non-small-cell lung carcinoma cells (EGFR$_1$ 19 exon mutation) | RPMI-1640 with 10% FBS |
| SK-OV-3 | Shanghai Institutes for Biological Sciences of the Chinese Academy of Sciences | Human ovarian carcinoma cells (EGFR$_2$ overexpressing) | Mycoy's 5A with 10% FBS |
| TT | Shanghai Institutes for Biological Sciences of the Chinese Academy of Sciences | Human thyroid carcinoma cells (RET C634W mutation) | F12K with 10% FBS |
| 3T3Swiss | Chinese Academy of Medical Sciences | Mouse fibroblasts (PDGFR overexpressing) | DMEM with 10% FBS |
| HCT116 | Chinese Academy of Medical Sciences | Human colon carcinoma cells | DMEM with 10% FBS |
| HUVEC | Invitrogen | Human umbilical vein endothelial cell (KDR overexpressing) | M200 with LSGS |
| Bel-7402 | Shanghai Institutes for Biological Sciences of the Chinese Academy of Sciences | Human hepatoma carcinoma cells | RPMI-1640 with 10% FBS |
| SGC7901 | Shenyang Pharmaceutical University | Human gastric carcinoma cells | RPMI-1640 with 10% FBS |
| CFPAC-1 | Chinese Academy of Medical Sciences | Human pancreatic carcinoma cells | IMDM with 10% FBS |
| A498 | Chinese Academy of Medical Sciences | Human renal carcinoma cells | MEM with 10% FBS |
| Eca109 | Shanghai Institutes for Biological Sciences of the Chinese Academy of Sciences | Human esophageal carcinoma cells | RPMI-1640 with 10% FBS |

Methods (MTT)

Cells in logarithmic growth phase were seeded at a certain density in a 96-well plate (200 μL/well). The cells were allowed to grow for 24 h and subsequently treated with different concentrations of drugs (including a blank group and a control group) and incubated for 72 h at 37° C. Each concentration in a given experiment was tested in triplicate. After 72 h of exposure, 20 μL of the MTT labeling reagent was added to the medium (the final concentration of MTT was 0.5 mg/mL), and the cells were incubated for additional 4 h at 37° C. Following this process, 180 μL of the medium was removed and 130 μL of DMSO was added to each well, or the medium was completely removed and 150 μL of DMSO was added to each well. Then the plate was shaken and mixed in a micro-oscillator. Finally the optical density (OD) of each sample was measured in a micro-plate reader at 550 nm. Cell inhibition rate was calculated according to the following formula:

$$\text{Inhibition}(\%) = \frac{OD_{control} - OD_{drug}}{OD_{control} - OD_{blank}} \times 100\%$$

According to cell inhibition rates, IC$_{50}$ was calculated by LOGIT method. The experiments were repeated twice and the data was expressed as means±SD. The present compounds were tested for the inhibition effects on the above cell lines, and the results were listed in table 2.

TABLE 2

| Compound | HCC827 | A431 | H292 | PC-9 | A375 | HT-29 | TT | HCT116 | SK-OV-3 |
|---|---|---|---|---|---|---|---|---|---|
| 19 | 0.1 | 1056.3 | 38.2 | 6.3 | 111.9 | 1663.9 | 109.6 | 561.3 | 1956.6 |
| 28 | 0.1 | 1356.1 | 66.6 | 9.3 | 108.5 | 1465.1 | 117.6 | 704.3 | 1832.1 |
| 29 | 0.6 | 2744.4 | 45.6 | 7.1 | 101.9 | 2170.2 | 126.9 | 651.7 | 2563.8 |
| 30 | 0.5 | 1570.3 | 43.2 | 7 | 196 | 2187.7 | 125.6 | 774.6 | 2499.1 |
| 37 | 0.6 | 1089.5 | 39.6 | 8.7 | 78.2 | 2502.6 | 134.1 | 562.2 | 2092.2 |
| 38 | 0.7 | 1455.8 | 45.2 | 7.7 | 178.3 | 2661.2 | 115.4 | 620.6 | 2060 |
| 39 | 0.2 | 2255.5 | 45.7 | 6.6 | 196.9 | 2874.5 | 186 | 509.8 | 1319.2 |
| 40 | 0.1 | 1560.4 | 56.4 | 7.8 | 246.8 | 2333.3 | 93 | 605.1 | 1189.2 |
| 1 | — | 1414.9 | — | — | — | 2822.2 | — | — | — |
| 2 | 5.6 | — | 46.3 | — | 185.3 | — | — | 1084.3 | — |
| 3 | — | — | — | — | — | — | — | 892.5 | 2016.4 |
| 5 | — | — | — | — | — | — | — | 1042.6 | — |
| 6 | 4.7 | 2099.3 | 46.9 | — | — | — | — | — | 2654.6 |
| 7 | 8.6 | — | — | — | — | — | — | — | — |
| 8 | — | — | — | — | — | — | — | — | 2774.3 |
| 12 | — | — | — | — | — | — | — | 1094.2 | — |
| 14 | 8.9 | — | 37.4 | — | 161.3 | — | — | 912.8 | 2884.3 |
| 15 | — | 2951.3 | — | — | — | — | — | — | — |
| 17 | 6.7 | — | — | — | — | — | — | — | — |
| 18 | — | — | — | — | — | — | — | 961.5 | — |
| 20 | 2.9 | 2140.5 | — | — | — | 2234.5 | — | — | — |
| 23 | 5 | — | — | — | — | — | — | — | 3365 |
| 24 | 5.6 | — | 81.8 | — | — | 1843 | — | — | 2446.5 |
| 25 | 2.6 | — | — | — | — | — | — | — | — |
| 26 | 1.4 | — | — | — | — | — | — | — | — |
| 27 | 4.6 | — | 78.3 | — | — | 2922.5 | — | — | — |
| 27 | 6.2 | — | — | — | — | — | — | — | — |
| 31 | 10.7 | — | — | — | — | — | — | — | — |
| 32 | 11 | — | — | 6.7 | — | — | — | — | — |
| 33 | 9.5 | — | 73.4 | 8.3 | — | — | — | — | — |
| 34 | 8.2 | — | 90.8 | 5.7 | — | — | — | — | — |
| 36 | — | — | — | — | — | — | — | — | 2924.6 |
| 41 | 0.9 | — | 89.9 | — | — | — | — | — | 2681.3 |
| 42 | 2.8 | — | — | — | — | — | — | — | — |
| 43 | 4.1 | — | — | — | — | — | — | — | — |
| 44 | 7.8 | 3567.4 | 124.1 | 16.8 | 315.4 | 3456.7 | 256.8 | 987.5 | 4025.6 |
| 45 | 9.7 | 4154.8 | 105.2 | 18.7 | 289.5 | 3412.5 | 3145 | 1056.7 | 4987.6 |
| Vandetanib | 19.3 | 3231.1 | 167.4 | 14.9 | 286.9 | 3225.6 | 191.7 | 1207.5 | 3510.2 |

| Compound | A549 | 3T3swiss | HUVEC | Bel-7402 | SGC7901 | CFPAC-1 | A498 | Eca109 |
|---|---|---|---|---|---|---|---|---|
| 19 | 1433.2 | 1086.7 | 21.2 | 3589.4 | 2756.1 | 4078.1 | 2057.1 | 4647.5 |
| 28 | 1915.6 | 1607 | 20.1 | 4897.5 | 3964.7 | 4471.5 | 2265.4 | 4878.6 |
| 29 | 2159.9 | 1366.2 | 23.8 | 5879.4 | 4454.7 | 5147.5 | 2364.8 | 5415.6 |
| 30 | 1506.1 | 1488.1 | 27.5 | 4568.4 | 4185.4 | 5154.4 | 2875.4 | 5524.8 |
| 37 | 1765.3 | 1545.7 | 29.5 | 5587.5 | 4015.4 | 5864.7 | 2156.8 | 5747.2 |
| 38 | 2356 | 1559.5 | 26.5 | 5936.5 | 3850.4 | 5786.4 | 2264.5 | 5925.4 |
| 39 | 2662.1 | 1747.5 | 18.8 | 5655.8 | 4524.1 | 5245.1 | 2314.4 | 5754.8 |
| 40 | 2404.4 | 1812.3 | 12.4 | 5879.8 | 3687.5 | 5324.5 | 2457.8 | 5457.2 |
| 1 | — | — | — | — | — | — | — | — |
| 2 | — | — | 40.4 | — | — | — | — | 5804.5 |
| 3 | — | — | — | — | — | — | — | — |
| 5 | — | — | — | — | — | — | — | — |
| 6 | 3926.2 | — | 37.6 | — | — | — | — | — |
| 7 | — | — | — | — | — | — | — | — |
| 8 | — | — | — | — | — | — | — | — |
| 12 | — | — | — | — | — | — | — | — |
| 14 | — | — | — | 5942.5 | — | — | 2727.5 | — |
| 15 | — | — | — | — | — | — | — | — |
| 17 | — | — | — | — | — | — | — | — |
| 18 | — | — | — | — | — | — | — | — |
| 20 | 2677.7 | 1724.6 | — | 5741.3 | — | — | — | — |
| 23 | 1405.2 | 2154.3 | — | — | — | — | — | — |
| 24 | 2943.3 | — | — | — | — | — | — | — |
| 25 | — | — | — | — | — | — | — | — |
| 26 | — | — | — | — | — | — | — | — |
| 27 | 3890.2 | — | — | — | — | — | — | — |
| 27 | — | — | — | — | — | — | — | — |
| 31 | — | — | — | — | — | — | — | — |
| 32 | 2704.4 | — | — | — | — | — | — | — |
| 33 | 3570.6 | — | — | — | — | — | — | — |
| 34 | 1290.2 | — | — | — | — | — | — | — |
| 36 | 3638.4 | — | — | — | — | — | — | — |
| 41 | 2713.8 | — | — | — | — | — | — | — |
| 42 | — | — | — | — | — | — | — | — |
| 43 | — | — | — | — | — | — | — | — |

TABLE 2-continued

Results for the present compounds in the In vitro cell experiment (IC$_{50}$, nM)

| 44 | 4897.6 | 2897.8 | 198.5 | 9684.5 | 5245.7 | 6718.4 | 3045.8 | 6984.7 |
|---|---|---|---|---|---|---|---|---|
| 45 | 5023.6 | 3789.5 | 186.7 | 6258.6 | 6258.6 | 6721.2 | 3147.2 | 7015.4 |
| Vandetanib | 4445.5 | 2527.4 | 71.7 | 6852.1 | 6852.1 | 6257.0 | 2961.5 | 6857.4 |

—: No data

Assay 2: In Vitro Enzyme Experiments

Terms

RET: A receptor involved in thyroid cancer
KDR: Human vascular endothelial growth factor receptor 2
FLT-1: Human vascular endothelial growth factor receptor 1
FGFR-1: Fibroblast growth factor receptor 1
EGFR: Human epidermal growth factor receptor 1
PDGFRβ: Platelet-derived growth factor receptor 13
BTK: Bruton tyrosine kinase
AXL: Anaplastic lymphoma kinase Methods:

ELISA: The enzyme plate was coated by enzyme reaction substrate (Poly (Glu, Tyr)$_{4:1}$) at a density of 20 μg/ml. Then the enzyme, the sample and 5 μM ATP were mixed in the well to react. After the reaction, the substrate phosphorylation was detected by anti-phosphotyrosine monoclonal antibody (4G10). In the next step, the goat-anti-mouse IgG linking with horse radish peroxidase (HRP) and tetramethylbenzidine (TMB) were added sequentially in the well to evaluate the level of substrate phosphorylation by the degree of color depth. In the experiment, a blank group without tyrosine kinase and a control group with the corresponding concentration of DMSO were established. Finally, 50 μL/well of H$_2$SO$_4$ at a concentration of 0.18M was added in each well to stop the reaction. The optical density (OD) of each sample was measured in a micro-plate reader at 450 nm.

$$\text{Inhibition rate} = \left(1 - \frac{OD_{drug} - OD_{blank}}{OD_{control} - OD_{blank}}\right) \times 100\%$$

The relative inhibition rate of the compound against tyrosine kinase protein was determined.

According to the inhibition rates at different concentrations, IC$_{50}$ was calculated by LOGIT method. The experiments were repeated three times, and the average of three IC$_{50}$ values was the final index to evaluate the ability of inhibition. The results were listed in Table 3.

Assay 3: Mouse Maximum Tolerated Dose (MTD) Experiment

In the mouse MTD experiment, the mice were administrated with the present compounds.

Healthy mice, having a small difference in body's weights, were chosen. The chosen mice were placed in different layers of cages according to their body's weights. In each layer, the mice were randomly divided into groups. In each group, there were three mice.

The administration dosages were 1000, 500, 250, 125, 62.5 and 31.25 mg/kg respectively and each two dosages differed by a factor of 2. For each of administration dosages, three mice were allotted. The mice were administrated with the present compounds for 7 days and then observed for the next 7 days without the present compounds.

Animal and Cage Labels
Cage Label:

The name of compound, the administration dosage and the animal group were labeled with a marker pen for each of cages.

Animal Label:

The mice in each group were labeled with picronitric acid. No. 1: left anterior, No. 2: left rear, and No. 3: right anterior.

Animal Weighing

The mice were weighed and recorded for each of groups.

Administration:

The present compounds were orally administered with the mice according to the administration dosage and the body weight.

Result: The maximum tolerated doses of the present compounds were listed in Table 4.

TABLE 4

The maximum tolerated dose of the present compounds

| Compound | MTD Level |
|---|---|
| 1 | B |
| 3 | B |
| 6 | A |

TABLE 3

Results for the present compounds in the in vitro enzyme experiments (IC$_{50}$, nM).

| Compound | RET | KDR | FLT-1 | FGFR-1 | EGFR | PDGFRβ | BTK | AXL |
|---|---|---|---|---|---|---|---|---|
| 19 | 9.1 | 10.6 | 25.6 | 15.7 | 66.3 | 112.6 | 219.8 | 1545.8 |
| 28 | 13.5 | 18.4 | 27.4 | 17.8 | 90.4 | 156.1 | 278.1 | 1467.2 |
| 29 | 13.4 | 17.4 | 30.8 | 24.6 | 126.8 | 246.3 | 259.7 | 1832.4 |
| 30 | 14.6 | 15.7 | 25.9 | 25.8 | 118.4 | 246.8 | 260.8 | 2009.4 |
| 37 | 15.8 | 15.9 | 30.4 | 27.7 | 98.5 | 188.9 | 311.5 | 1715.4 |
| 38 | 19.8 | 17.6 | 35.6 | 28.9 | 100.5 | 267.8 | 325.2 | 2154.4 |
| 39 | 10.2 | 18.9 | 34.6 | 19.6 | 121.4 | 258.1 | 297.4 | 2045.8 |
| 40 | 17.3 | 18.7 | 39.8 | 28.4 | 112.5 | 240.6 | 306.5 | 1985.7 |
| Vandetanib | 21.4 | 23.9 | 47.8 | 38.3 | 144.9 | 316.8 | 366.2 | 2363.3 |
| 44 | 23.4 | 40.5 | 51.2 | 39.8 | 156.5 | 306.5 | 424.1 | 2990.4 |
| 45 | 27.5 | 38.6 | 50.1 | 41.6 | 159.4 | 328.5 | 414.2 | 2987.5 |

TABLE 4-continued

The maximum tolerated dose of the present compounds

| Compound | MTD Level |
|---|---|
| 7 | E |
| 14 | E |
| 17 | B |
| 19 | C |
| 20 | D |
| 24 | D |
| 27 | B |
| 28 | C |
| 29 | D |
| 30 | C |
| 32 | B |
| 33 | E |
| 34 | D |
| 37 | C |
| 38 | D |
| 39 | E |
| 40 | D |

A: >1000 mg/kg;
B: >500 mg/kg and ≤1000 mg/kg;
C: >250 mg/kg and ≤500 mg/kg;
D: >125 mg/kg and ≤250 mg/kg;
E: >62.5 mg/kg and ≤125 mg/kg;
F: >31.25 mg/kg and ≤62.5 mg/kg;
G: ≤31.25 mg/kg.

What is claimed is:

1. A method for the treatment of cancer comprising administering a therapeutically effect amount of a compound or a pharmaceutically acceptable salt thereof, or a pharmaceutical composition containing the compound or a pharmaceutically acceptable salt thereof to a subject having cancer;

wherein the cancer is selected from the group consisting of thyroid cancer, melanoma, colon cancer, gastric carcinoma, and esophagus cancer, wherein said compound is a compound of formula (I):

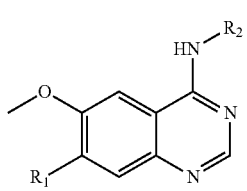

(I)

wherein $R_1$ is —O(CH$_2$)$_n$R$_3$, wherein n is 3, 4 or 5, and $R_3$ is —NR$^e$R$^f$, wherein R$^e$ and R$^f$ are each independently selected from the group consisting of C$_{1-6}$alkyl, or R$^e$ and R$^f$ are taken together to form —(CH$_2$)$_4$—; and R$^2$ is

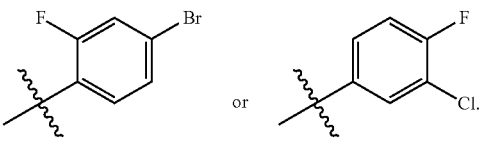 [SMILES: *c1ccc(Br)cc1F ; "or" ; *c1ccc(F)c(Cl)c1]

2. The method of claim 1, wherein R$^e$ and R$^f$ are methyl.

3. The method of claim 2, wherein R$_1$ is selected from:

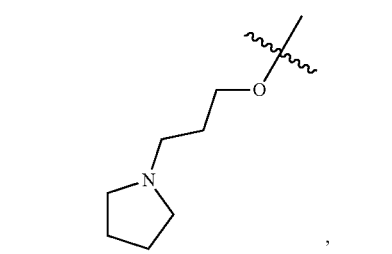

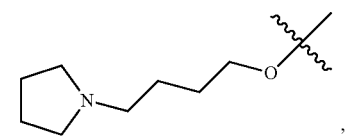

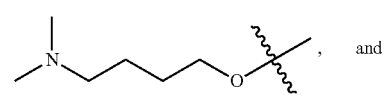

, and

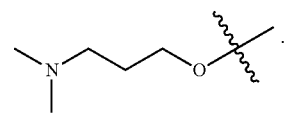

.

4. The method of claim 1, wherein said compound is selected from the group consisting of:

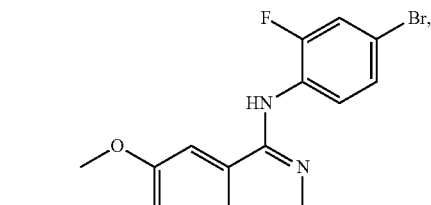

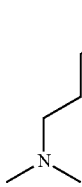

-continued

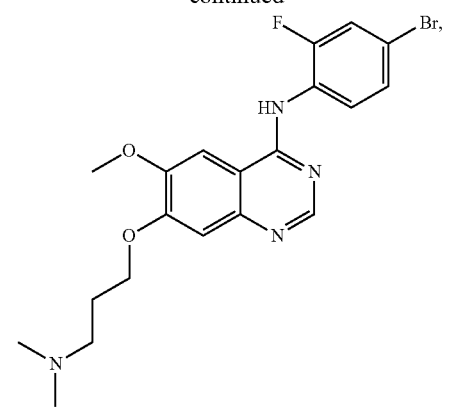

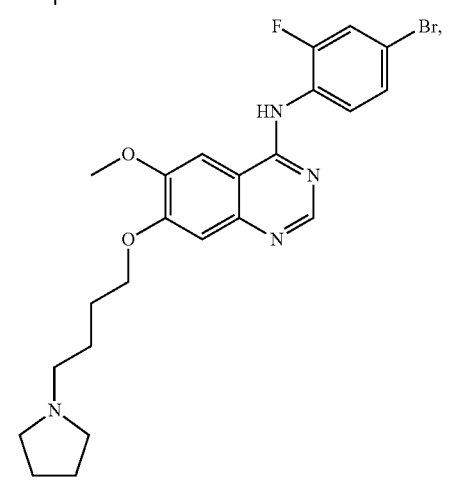

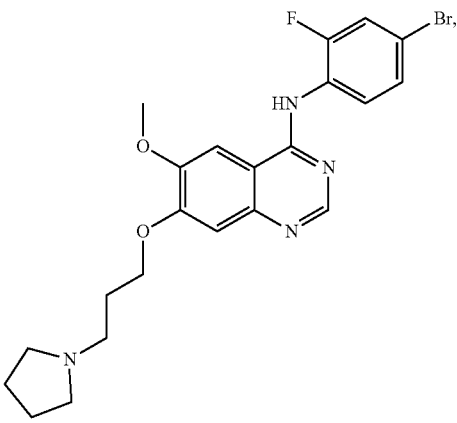

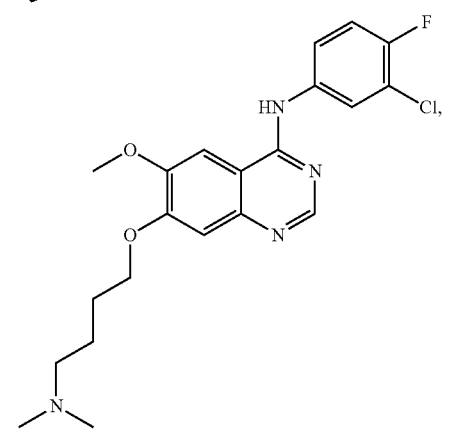

-continued

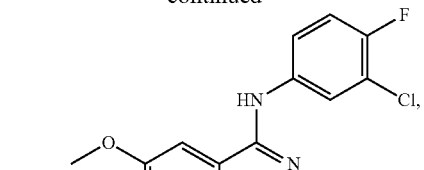

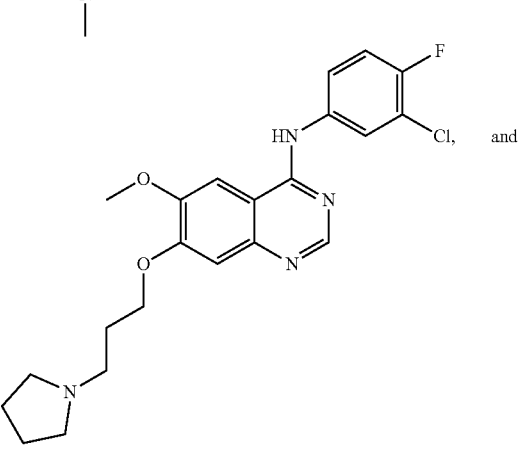

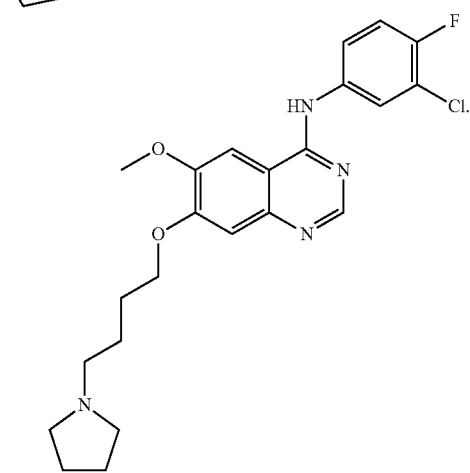

5. The method of claim 4, wherein the cancer is selected from the group consisting of
thyroid cancer caused by RET C634W mutation,
melanoma caused by KDR expressing, and
colon cancer caused by expressing both c-KIT and PDGFR.

6. A method for inhibiting the activity of a cell, comprising contacting a compound or a pharmaceutically acceptable salt thereof, or a pharmaceutical composition containing the compound or a pharmaceutically acceptable salt thereof with the cell, wherein said compound is a compound of formula (I):

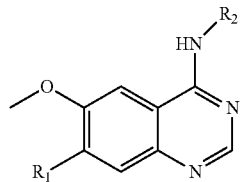

wherein

R₁ is —O(CH₂)ₙR₃, wherein n is 3, 4 or 5, and

R₃ is —NR^eR^f, wherein R^e and R^f are each independently selected from the group consisting of C₁₋₆alkyl, or R^e and R^f are taken together to form —(CH₂)₄—; and R² is

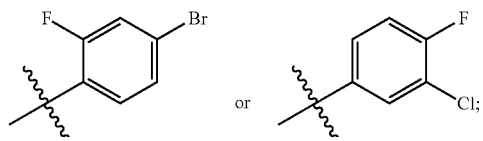 [SMILES: *c1ccc(Br)cc1F ; *c1ccc(F)c(Cl)c1]

wherein the cell is a human colon carcinoma cell, human epidermoid carcinoma cell, human esophageal carcinoma cell, human gastric carcinoma cell, human hepatoma carcinoma cell, human lung carcinoma cell, human melanoma cell, human non-small-cell lung carcinoma cell, human ovarian carcinoma cell, human pancreatic carcinoma cell, human renal carcinoma cell, human thyroid carcinoma cell, or human umbilical vein endothelial cell.

7. The method of claim 6, wherein R^e and R^f are methyl.

8. The method of claim 7, wherein R₁ is selected from:

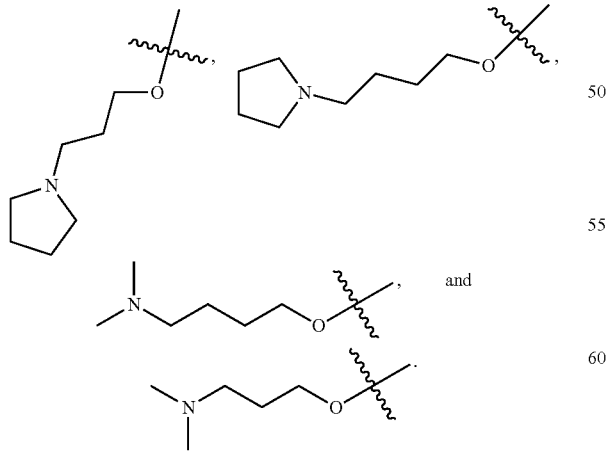

9. The method of claim 6, wherein said compound is selected from the group consisting of:

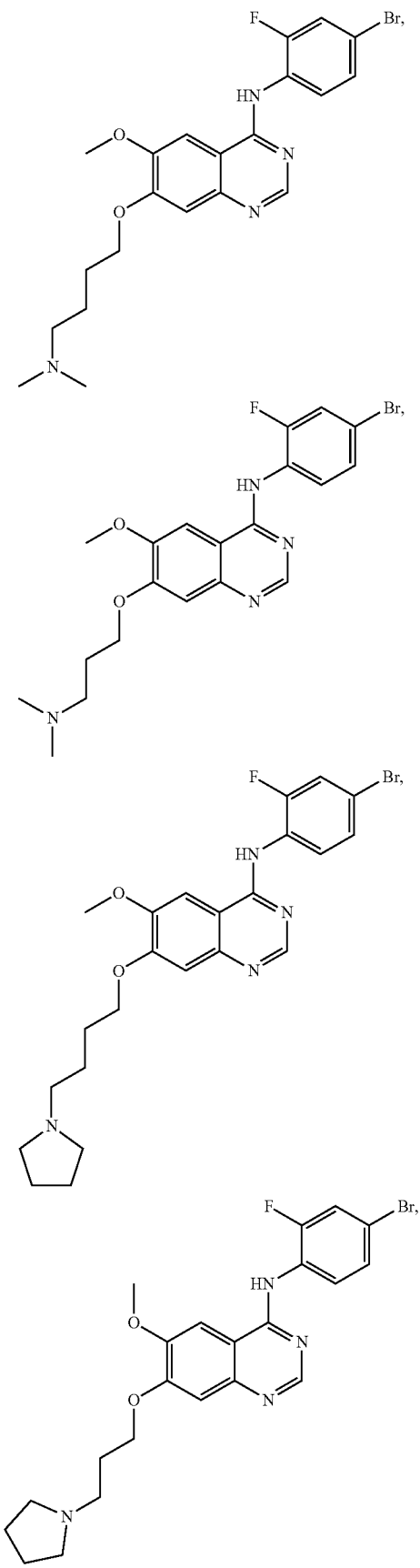

69
-continued
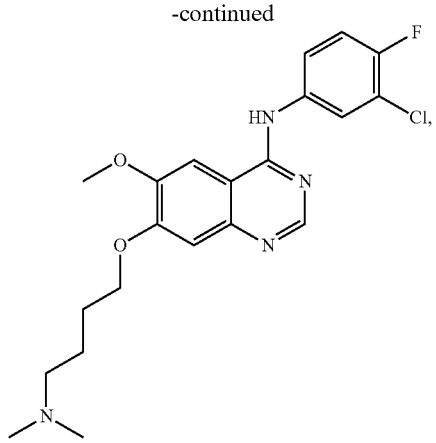
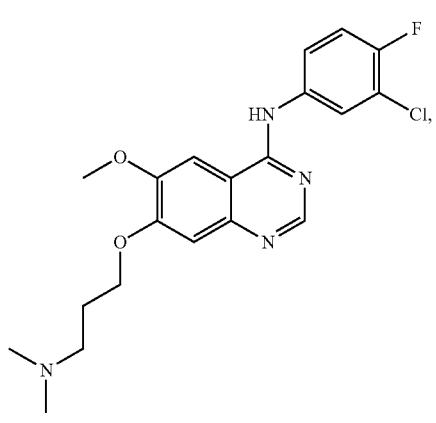
70
-continued
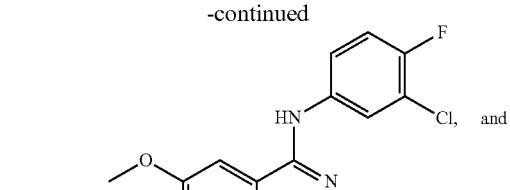
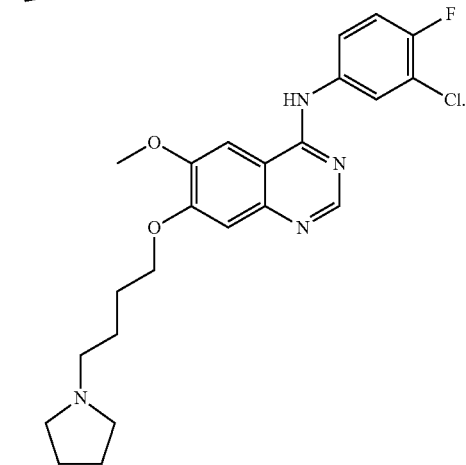
* * * * *